United States Patent
Ding et al.

(10) Patent No.: US 7,226,931 B2
(45) Date of Patent: Jun. 5, 2007

(54) (R/S) RIFAMYCIN DERIVATIVES, THEIR PREPARATIONS AND PHARMACEUTICAL COMPOSITIONS

(75) Inventors: Charles Z. Ding, Plano, TX (US); Zhenkun Ma, Dallas, TX (US); Jing Li, Dallas, TX (US); Susan Harran, Dallas, TX (US); Yong He, Arlington, TX (US); Keith P. Minor, Dallas, TX (US); In Ho Kim, Lewisville, TX (US); Jamie C. Longgood, Carrollton, TX (US); Yafei Jin, Dallas, TX (US); Keith D. Combrink, Fort Worth, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 66 days.

(21) Appl. No.: 11/186,425

(22) Filed: Jul. 21, 2005

(65) Prior Publication Data

US 2006/0019986 A1 Jan. 26, 2006

Related U.S. Application Data

(60) Provisional application No. 60/590,190, filed on Jul. 22, 2004.

(51) Int. Cl.
  *C07D 498/08* (2006.01)
  *A61K 31/4709* (2006.01)
  *A61P 31/04* (2006.01)

(52) U.S. Cl. .................... 514/306; 540/458; 548/138; 548/208

(58) Field of Classification Search ............... 540/458; 546/138, 208; 514/306
  See application file for complete search history.

(56) References Cited

FOREIGN PATENT DOCUMENTS

| WO | WO 94/28002 | 12/1994 |
|---|---|---|
| WO | WO 03/045319 A2 | 6/2003 |
| WO | WO 2005/070940 A2 | 8/2005 |
| WO | WO 2005/070941 A1 | 8/2005 |

OTHER PUBLICATIONS

Brufani M, Cerrini S, Fedeli W, Vaciago A. Rifamycins: an insight into biological activity based on structural investigations. J Mol Biol. Aug. 15, 1974;87(3):409-35.

Farr, BM. Rifamycins, in Principles and Practice of Infectious Diseases. Mandell GL, Bennett JE, Dolin R, Eds. Churchhill Livingstone Philadelphia pp. 348-361.
Li Q, Mitscher LA, Shen LL. The 2-pyridone antibacterial agents: bacterial topoisomerase inhibitors. Med Res Rev. Jul. 2000;20(4):231-93.
PCT Notification of Transmittal of the International Search Report and the Written Opinion of the International Searching Authority, or the Declaration. Dec. 12, 2005.

*Primary Examiner*—Bruck Kifle
(74) *Attorney, Agent, or Firm*—Jackson Walker L.L.P.

(57) ABSTRACT

Rifamycin derivatives having the following structure of general formula I (both hydroquinone and corresponding quinone ($C_1$-$C_4$) forms):

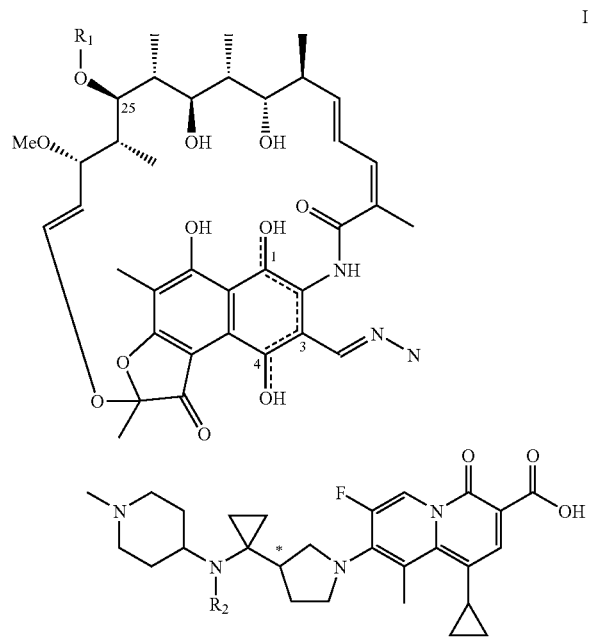

or its salts, hydrates or prodrugs thereof; wherein a preferred $R_1$ comprises hydrogen or acetyl and a prefered $R_2$ comprises hydrogen, methyl or other lower alkyls; wherein asterik (*) denotes the carbon bearing the chiral center, wherein absolute configuration is assigned as R or S. Methods of preparation of the aforementioned rifamycin derivatives are also described. The compounds exhibit antimicrobial activities, including activities against drug-resistant microorganisms.

15 Claims, 3 Drawing Sheets

Scheme A: Preparation of the compounds of formula I.

1.Scheme C: Preparation of the compounds of formula (BF1).

(R/S) RIFAMYCIN DERIVATIVES, THEIR PREPARATIONS AND PHARMACEUTICAL COMPOSITIONS

BACKGROUND

This application claims priority to U.S. Provisional Patent Application Ser. No. 60/590,190, entitled "4H-4-Oxoquinolizine Derivatives Having Improved Target Selectivity," filed on Jul. 22, 2004, the entire content of which is hereby incorporated by reference.

This invention relates to compounds of rifamycin origin having antimicrobial activities, their compositions, methods of preparation, and methods for treatment or prevention of infectious disease. More particularly, the rifamycin derivatives of the current invention comprise a rifamycin moiety covalently linked to a linker at the C-3 carbon of the rifamycin moiety and the linker is, in turn, covalently linked to a 4H-4-oxoquinolizine moiety. The invention pertains to the preferred chirality of the linker at its pro-chiral carbon center, which contributes to the antibacterial activities of the compounds. This invention also encompasses chemical processes that address the chirality of the linker and the synthesis of the compounds. The rifamycin derivatives of the present invention are active against drug-resistant microorganisms with reduced frequency of developing mutational resistance.

Rifamycins are natural products with potent antimicrobial activity. Examples of the naturally-occurring rifamycins are rifamycin B, rifamycin O, rifamycin R, rifamycin U, rifamycin S, rifamycin SV and rifamycin Y (Brufani, M., Cerrini, S., Fedeli, W., Vaciago, A. *J. Mol. Biol.* 1974, 87, 409-435). The therapeutic applications of the naturally-occurring rifamycins are limited due to their poor pharmacokinetics and oral bioavailability, weak activity against Gram-negative pathogens and low distribution into the infected tissues. Chemical modifications result in many semi-synthetic rifamycin derivatives with improved spectrum and pharmacological profiles. Among the semi-synthetic compounds, rifampin, rifabutin and rifapetine have been developed into therapeutic agents and are currently used for the treatment of tuberculosis and other microbial infections (Farr, B. M. Rifamycins, in *Principles and Practice of Infectious Diseases*; Mandell, G. L., Bennett, J. E., Dolin, R., Eds.; Churchhill Livingstone: Philadelphia; p348-361).

One major liability associated with the current rifamycin class of antimicrobial agents, such as rifampin, however, is their rapid development of microbial resistance. Mutations in their antibacterial target RNA polymerase are mainly responsible for the high frequency of microbial resistance to rifamycins. Thus, there is a need to have new compounds addressing the rifamycin liability. The compounds of the present invention are chemically designed to address drug resistance to both the rifamycin and quinolone class of antibiotics by chemically linking rifamycin and quinolone antibacterial pharmacophores together through a stable bivalent linker. The novel inventive rifamycin compounds exert their antimicrobial activity through multiple antibacterial mechanisms targeting bacterial RNA polymerase, DNA gyrase and DNA topoisomerase IV, and, therefore, they exhibit reduced frequency of resistance, and slow or eliminate development of drug resistance.

Reference is made to PCT application WO 03/045319 A2 that discloses rifamycin derivatives formed by linking rifamycin and a therapeutic drug and the use of them as vehicles for delivering the therapeutic drug.

However, this reference does not describe any drug that is introduced to the C-3 position of a rifamycin molecule. The reference also fails to demonstrate by example that a quinolone antibiotic or its pharmacophore structure is linked to any position of rifamycin molecule.

SUMMARY

One aspect of the current invention relates to a compound of general formula I (either hydroquinone or corresponding quinone ($C_1$-$C_4$) forms):

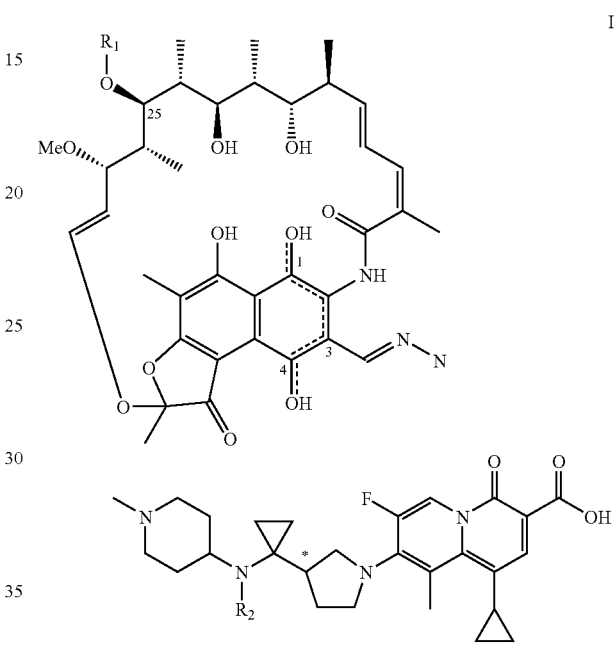

or its salts, hydrates or prodrugs thereof, wherein, a preferred $R_1$ comprises hydrogen or acetyl; a prefered $R_2$ comprises hydrogen, methyl or other lower alkyls; wherein the asterik (*) denotes the carbon bearing the chiral center, wherein absolute configuration is assigned as R or S.

These novel compounds exhibit antibiotic properties. They can be used in the control or prevention of infectious diseases in mammals, both humans and non-humans. In particular, they exhibit a pronounced antibacterial activity, even against multiresistant strains of microbes, for example quinolone and rifamycin resistant strains. The compounds can also be administered in combination with known antibacterial substances, exhibiting synergistic effect, examples of known antibacterial substances include those from the beta-lactam class, such as ceftriaxone; oxazolidinone class, such as linezolid; antibacterial peptides, such as vancomycin, dalbavancin, daptomycin; and polymycin B.

The compounds of general formula (I) have a chiral center marked by the asterisk (*), which can have either (R) or (S) configurations. This invention also discloses a novel chemical process for the preparation of both forms (R/S) of the compounds in general formula (I).

DETAILED DESCRIPTION OF THE INVENTION

Figure 1:
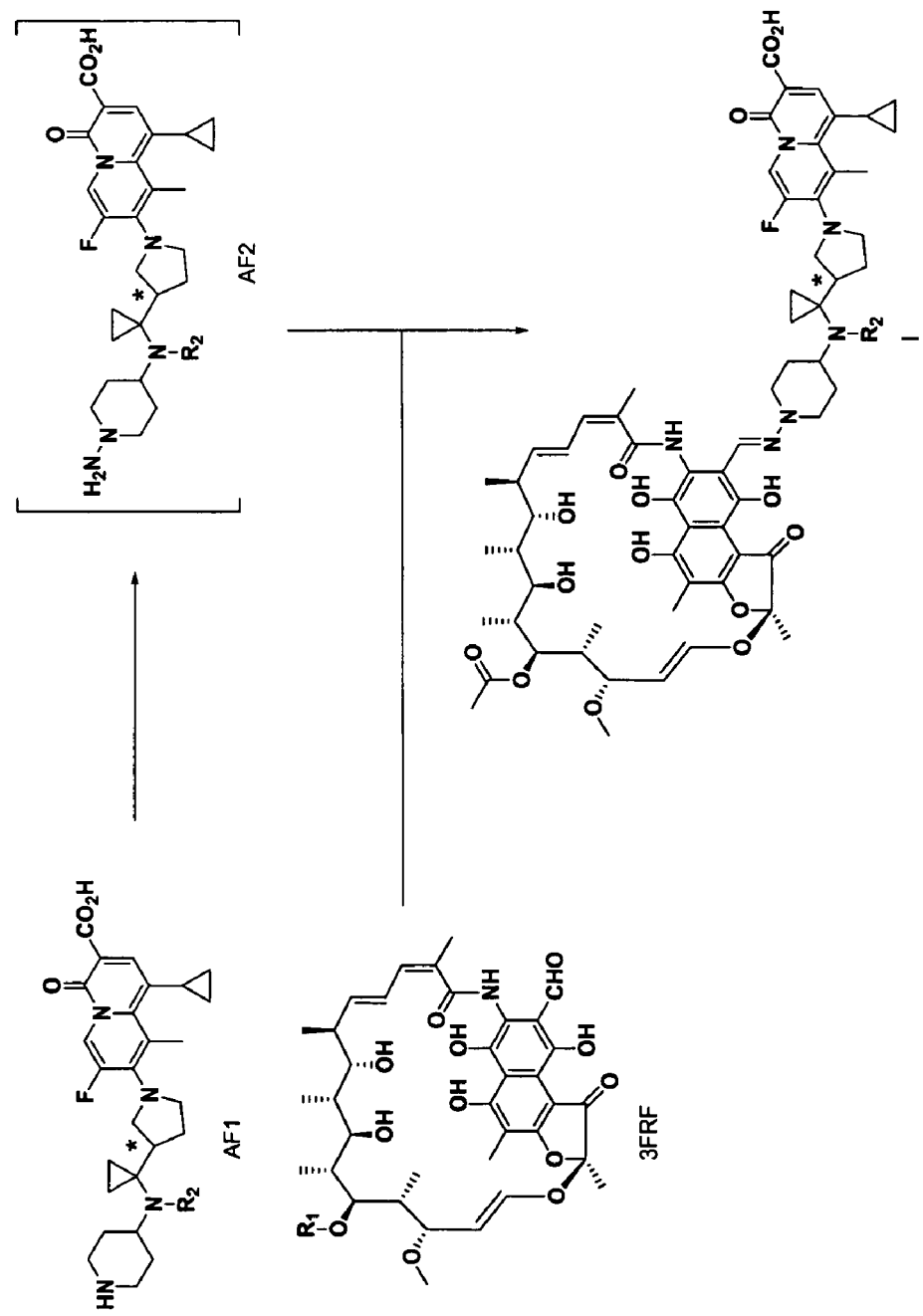
FIG. 1 shows Scheme A for the preparation of the compounds of formula I.
Figure 2:
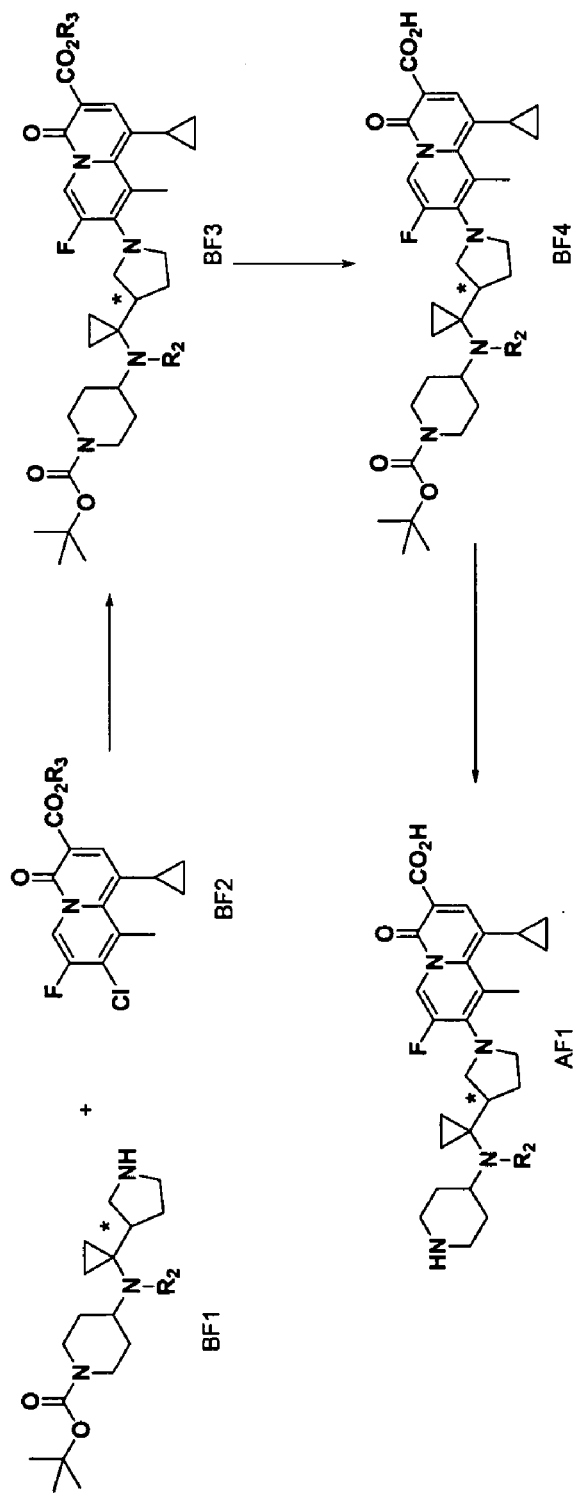
FIG. 2 shows Scheme B for the preparation of the compounds of formula (AF1).
Figure 3:
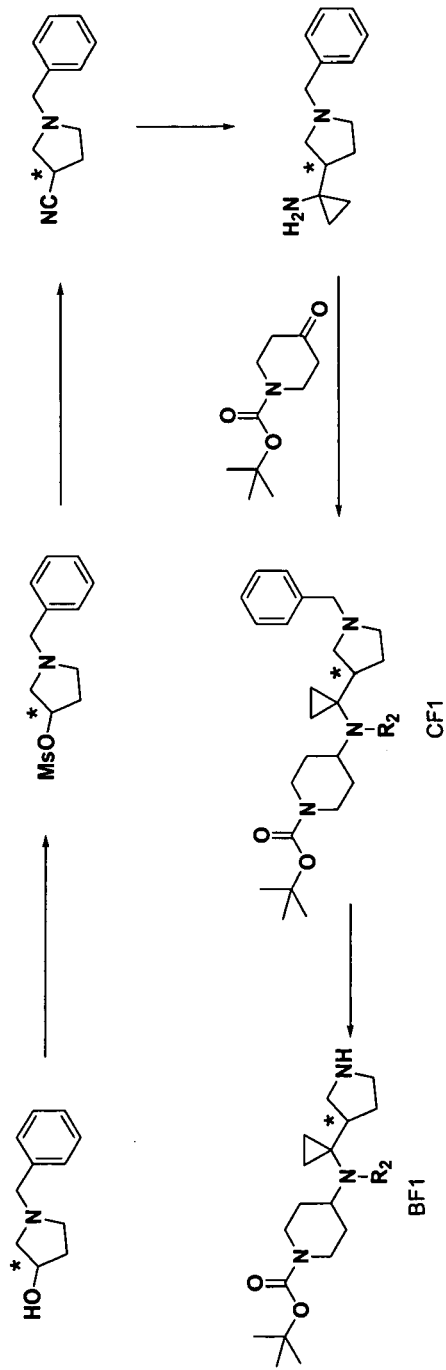
FIG. 3 shows Scheme C for the preparation of the compounds of formula (BF1).

One aspect of the present invention pertains to a compound of general Formula I (both hydroquinone and corresponding quinone ($C_1$-$C_4$) forms):

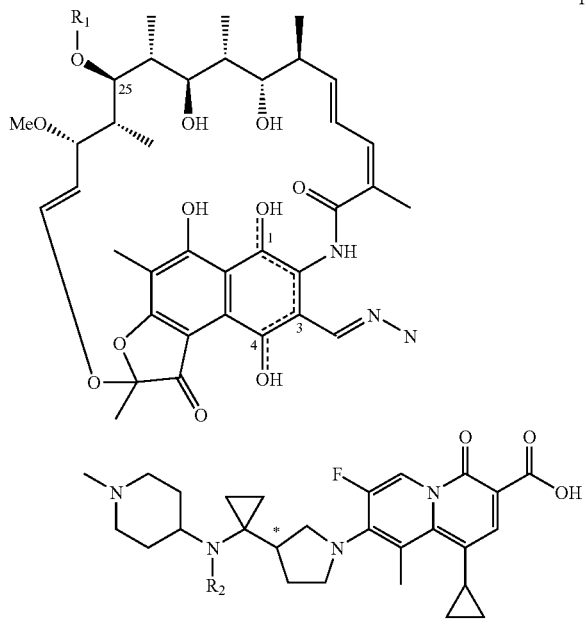

or its salts, hydrates or prodrugs thereof;
wherein:
$R_1$ comprises hydrogen or acetyl,
$R_2$ comprises hydrogen, methyl, or other lower alkyls of from 2 to 10 carbons.

wherein asterik (*) denotes the carbon bearing the chiral center, wherein absolute configuration is assigned as R or S.

These compounds are novel exhibit antibiotic properties. They can be used in the control or prevention of infectious diseases in mammals, both humans and non-humans. In particular, they exhibit a pronounced antibacterial activity, even against multiresistant strains of microbes, in particular rifampin-resistant and quinolone-resistant *Staphylococcus aureus*. The compounds can also be administered in combination with known antibacterial substances, exhibiting synergistic effects, examples of the antibacterial substancesinclude those from the beta-lactam class, such as cephotrizole; oxazolidinone class, such as Linazolid; antibacterial peptides, such as vancomycin, dalbavancin, daptomycin; and polymycin B.

One object of the present invention is to provide compounds of formula I, their readily hydrolyzable prodrug forms, for example, esters, and pharmaceutically acceptable salts thereof, and for use as therapeutically active substances; medicaments based on these substances; optionally in combination with other class of antibiotics and their production; the use of these substances as medicaments and for the production of active antibacterial medicaments; as well as the preparation of the compounds of formula I and their pharmaceutically acceptable salts and intermediates.

The term "lower alkyl" denotes the number of carbon atoms in the group in question is not more than 10. Examples of preferred lower alkyls include methyl, ethyl, propyl, isopropyl, n-butyl and isomers thereof and n-pentyl and isomers thereof. Cyclopropyl, cyclobutyl, cyclopentyl and cyclohexyl are also examples of lower alkyls. The akyl group of this invention can be optionally substituted with 1-3 substitutents.

The term "hydrate" as used herein, refers to a molecule that has been hydrated, or reacted with water in a hydration reaction. In a hydration reaction, molecules of water react with a compound, but the H—OH bond is not split. The water is usually split off from the hydrated compound by heat, yielding the anhydrous compound.

The term "prodrugs" as used herein refers to the prodrugs of the compounds of the current invention which are suitable for use in humans and animals with acceptable toxicity, irritation, allergic response, and the like, commensurate with a reasonable benefit to risk ratio, and effective for their intended use. The term "prodrugs" as used herein, represents compounds which can be transformed in vivo to active compounds of the formula (I) defined above.

The term "salt" as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of salts are salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

A preferred group of compounds of formula (1) comprises those in which $R_1$ is H or acetyl; $R_2$ is H or methyl. The most preferred compounds are those in which $R_1$ is H or acetyl, $R_2$ is H or methyl in their hydroquinone form, where asterisk (*) denotes (R)-chiral configuration.

Specifically, one aspect of the present invention relates to the following compounds: (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV, (S)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV, (R/S)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV, (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1- ylimino)-methylenyl]-rifamycin S, (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-25-deacetyl-rifamycin SV, or (R)-3-[(4-{1-[1-(3-carboxy-1-cyclopropyl-7-fluoro-9-methyl-4-oxo-4H-quinolizine-8-yl)-pyrrolidin-3-yl-cyclopro pyl]-amino}-piperidin-1-ylimino)-methylenyl]-rifamycin SV.

The compounds of formula (I) can be prepared in accordance with the process as shown in Scheme A below, wherein $R_1$, $R_2$ and asterisk (*) denote the same as above and through out of this specification.

Scheme A: Preparation of the copmpounds of formula I.

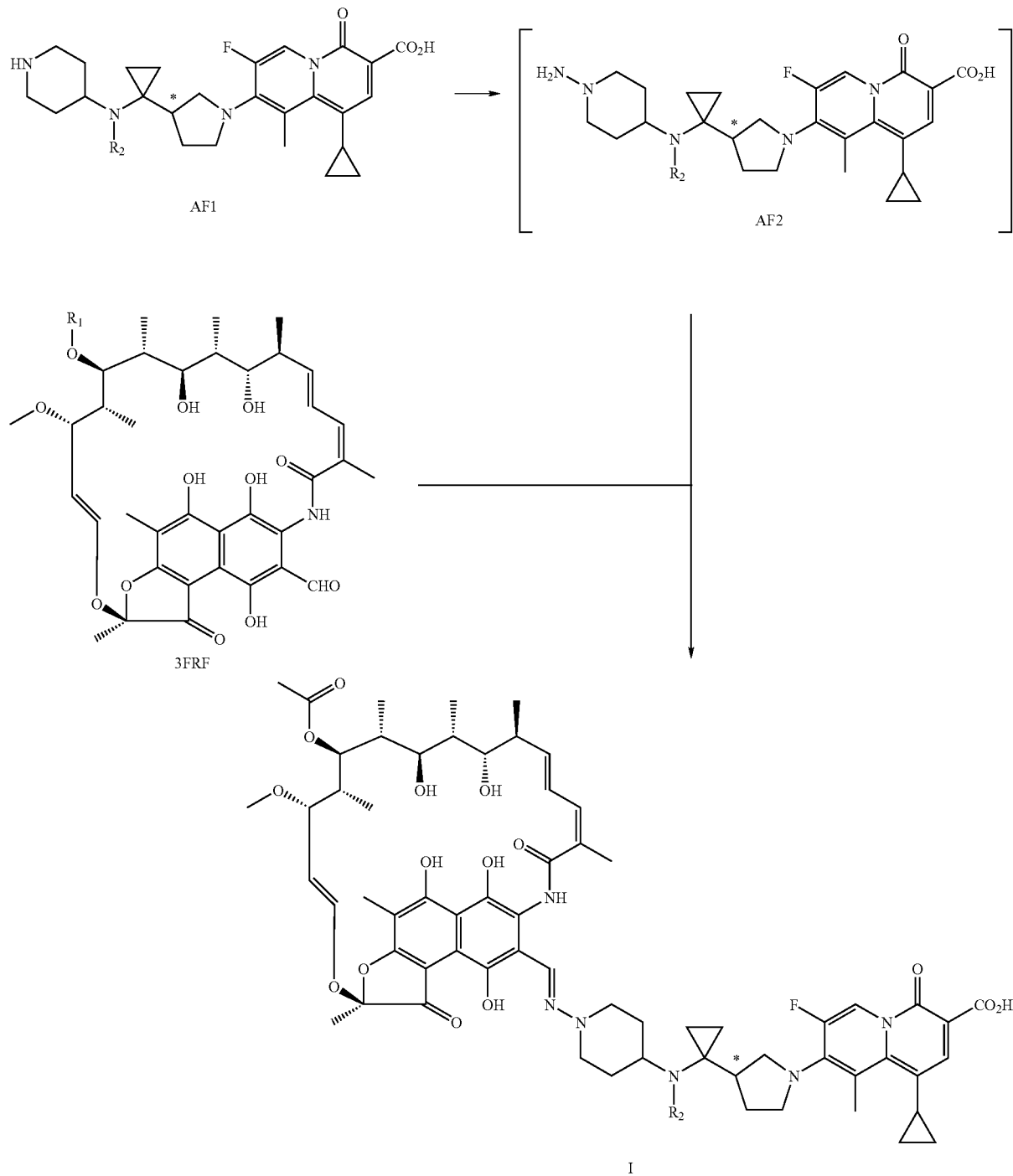

The process involves coupling of a hydrazine of formula (AF2) to 3-formylrifamycin of formula (3FRF) in a solvent, such as water, ethanol, methanol, THF, acetone, acetic acid, or a mixture thereof at a temperature from 0 to 50° C. The optional additives are, but not limited to, NaOH, ascorbic acid or its salt, and sodium acetate. The hydrazine of the formula (A2) can be in its free base form or its acid salts, such as, HCl. The hydrazine can be prepared in situ from a diaminoacid of formula (AF1) using amination reagents, such as $H_2NOSO_3H$, in an alkaline solvent, such as aqueous 1N NaOH.

Both hydrazine of formula (AF2) and its precursor diaminoacid of formula (AF1) and their enantiomers are novel. The preparation of the diaminoacid of formula (AF1) is illustrated in Scheme B ($R_3$ is H or lower alkyls).

triamine with a known 4H-4-oxoquinolizine of the formula (BF2), which can be prepared according to a known process (see Li, Qun. et al, Hetereocycles, 1999, Vol. 51, 1345-1353), in a solvent, such as acetonitrile, in the presence of a base, such as $NaHCO_3$, at temperature of between 20 to 100° C., produces compounds of formula (BF3). Hydrolysis, if necessary, can be accomplished by a base, such as LiOH, in an alcoholic solvent, such as ethanol, to generate compounds of formula (BF4). The protecting group can be conveniently removed using acids, such as trifluoroacetic acid, to produce compounds of formula (AF1).

The protected triamine of formula (BF1) and compounds of formula (BF3), (BF4) and their enantiomers are also novel. The preparation of the protected triamine of formula (BF1) is illustrated in Scheme C.

Scheme B: Preparation of the compounds of formula (AF1).

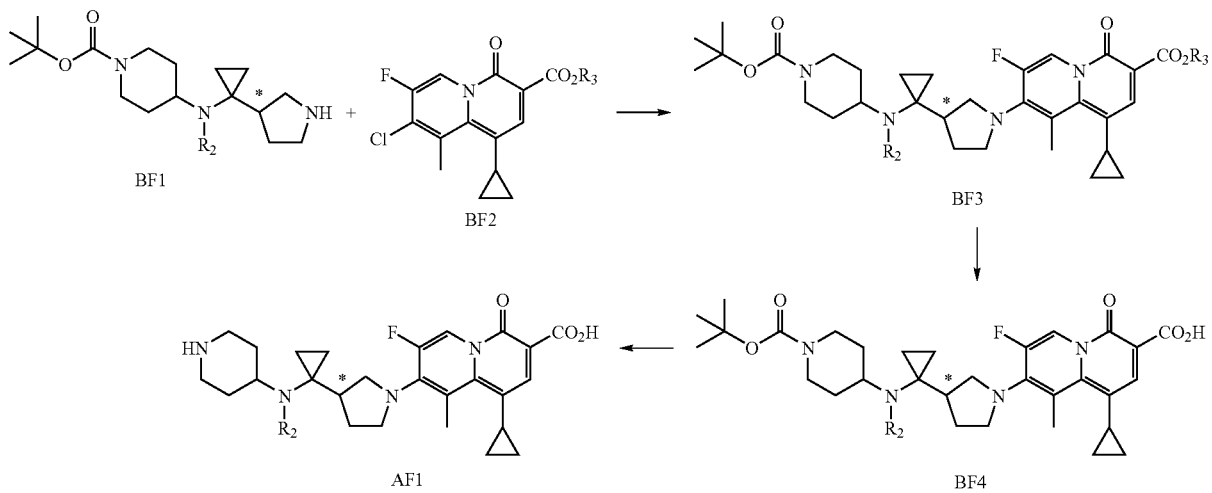

The diaminoacid of formula (AF1) can be prepared from selectively protected triamine of formula (BF1). Reaction of Scheme C: Preparation of the compounds of formula (BF1

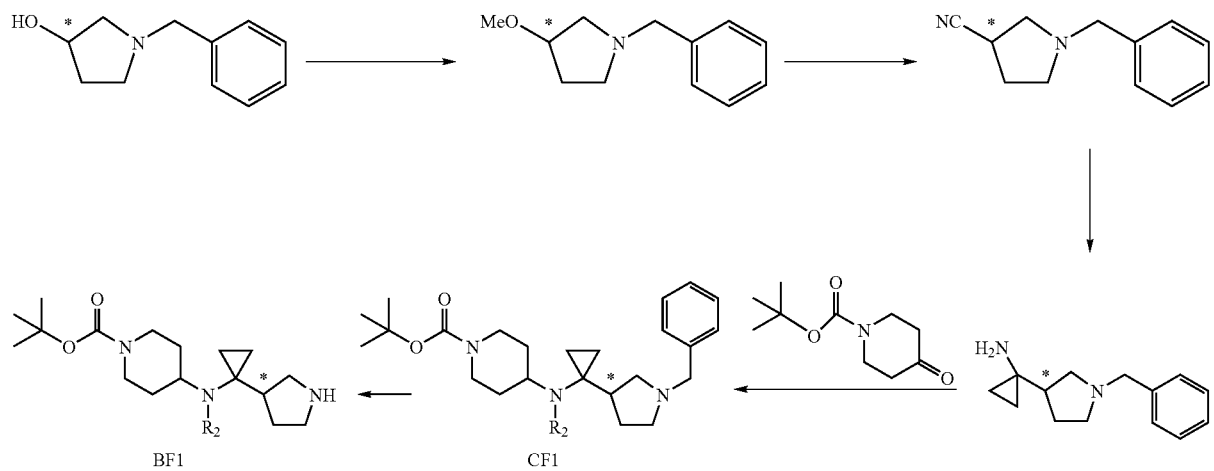

The preparation of triamine of formula (BF1) can be achieved by reacting commercially available 1-benzyl-3-hydroxypyrrolidine. Both R and S-enantiomers of 1-benzyl-3-hydroxypyrrolidine are available commercially. The R and S-enantiomers of the formula (BF1) can be prepared starting from either S or R-enantiomers of 1-benzyl-3-hydroxypyrrolidine. The inversion of the stereochemistry occurs at cyano displacement reaction, which is the stage that sets the absolute configuration of the triamine. Accordingly, 1-benzyl-3-hydroxypyrrolidine can be converted to its mesylate using a mesylating agent, such as mesyl chloride or mesyl anhydride, in the presence of a base, such as triethylamine, in a solvent, such as toluene or ethyl acetate. The subsequent cyano replacement of the mesylate can be done using a cyanide, such as tetrabutylammonium cyanide, triethylbenzylammonium cyanide, or minerial cyanides, such as sodium cyanide, in the presence of a phase transfer catalyst, such as tetrabutylammonium cyanide in solvent, such as acetonitrile, or DMSO, at a temperature of from about 20° C. to about 70° C. The cyclopropanation reaction to give cyclopropylamine can be accomplished using ethylmagnesium bromide in the presence of titanium tetra-isopropoxide, followed by treatment with a Lewis acid, such as $BF_3$ etherate. The reaction can be done in a solvent, such as THF, ether, or dioxane, or a mixture of them, at temperature ranging from about −78° C. to room temperature. This process of producing cyclopropylamine is enantioselective, and enantioselectivity of the cyclopropylamine may vary from 80% ee to high of greater than 95% ee. Reductive amination of the cyclopropylamine with N-BOC 4-piperidone, followed by addition of an aldehyde using reductive hydride, such as sodium triacetoxyborohydride, in a solvent, such as THF, dichloromethane, acetic acid, or a mixture thereof, produces compounds of formula (CF1). The hydrogenative debenzylation reaction can be achieved using a palladium catalyst, such as 10% palladium on charcoal, or 20% palladium hydroxide in solvent, such as ethanol, methanol, acetic acid, or a mixture thereof, the hydrogen pressure can be in an atmosphere of 60-100 PSI. All the amines can be converted to their acid salts by addition of acids, such as HCl, acetic acid, $MeSO_3H$, etc.

The cyclopropylamine and compounds of formula (CF1) and their enantiomers and their corresponding salts also are novel.

The compounds of formula I which may contain a basic moiety, such as, but not limited to, an amine, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which may contain an acidic moiety, such as, but not limited to, a carboxylic acid, may form salts with a variety of organic and inorganic bases. Exemplary basic salts include ammonium salts, alkali metal salts, such as sodium, lithium, and potassium salts, alkaline earth metal salts, such as calcium and magnesium salts, salts with organic bases (for example, organic amines) such as benzathines, dicyclohexylamines, hydrabamines (formed with N,N-bis(dehydro-abietyl)ethylenediamine), N-methyl-D-glucamines, N-methyl-D-glucamides, t-butyl amines, and salts with amino acids, such as arginine, lysine, and the like. Basic nitrogen-containing groups may be quaternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl and stearyl chlorides, bromides, and iodides), arylalkyl halides (e.g., benzyl and phenethyl bromides), and others.

Individual stereoisomers of the compounds of this invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

In addition, compounds of formula (I) may have prodrug forms. Any compound that will be converted in vivo to provide the bioactive agent (i.e., a compound of Formula I) is a prodrug. For example, pro-drug compounds of Formula I may be carboxylate ester moieties. A carboxylate ester may be conveniently formed by esterifying the carboxylic acid or generated in a separate preparation.

The compounds of formula I are rifamycin derivatives, both hydroquinone and its quinone form at C-1 and C-4. Formula I is labeled at the C-1, C-3, C-4 and C-25 positions for illustration purposes. The hydroquinone and quinone forms of the compounds of formula I are different in their oxidation states and can be transformed from one to another by utilizing an oxidation or reduction reaction affected by reagents, such as ascorbic acid, or potassium permanganate ($KMnO_4$).

Biological Activity:

As already mentioned, the compounds of formula I or their salts have antibacterial properties and activities against rifampin and quinolone resistant strains. They showed activity against a large number of pathogenic microorganisms e.g. *Staphylococcus aureus, S. pneumoniae, H. influenzae* etc. Representative compounds of the formula (I) were assayed for antimicrobial activity as follows: Minimum Inhibitory Concentrations (MICs) were determined by the microbroth dilution method as per NCCLS guidelines (National Committee for Clinical Laboratory Standards, 2000). All growth incubations were conducted at 37° C. Bacterial cultures were tested in the following bacteriological media: *S. aureus, S. epidermidis* in Cation-Adjusted Mueller-Hinton Broth, *S. pneumoniae* in THY Broth supplemented with 1 mg/mL catalase under 5% $CO_2$ atmosphere, *S. pyogenes* in THY Broth, *E. faecalis* in BHI Broth, *H. influenzae* in BHI Broth supplemented with 0.75 µL of 1 mg/mL NAD and 150 µL of 1 mg/ml hematin per 5 mL. The antimicrobial activities of the examples of the current invention are shown in Table 1.

S. aureus ATCC 29213, S. epidermidis ATCC 12228, S. pneumoniae ATCC6303, S. pyogenes ATCC 19615 and E. faecalis ATCC 29212 are rifampin-susceptible Gram-positive strains. Rifampin exhibits excellent activity against these organisms with MICs between 0.008 and 1 μg/ml. The compounds of the current invention show similar activity against these strains. H. influenzae ATCC 10211 is Gram-negative bacteria. Rifampin has intrinsically weaker activity against these organisms with MICs between 0.24 and 16 μg/ml. Compounds of the current invention demonstrate similar activity against these strains. Most importantly, compounds of the current invention demonstrate excellent activity against rifampin-resistant organisms. S. aureus ATCC 29213 RpoB$^{D417Y}$ is a high level rifampin-resistant strain due to a RNA polymerase mutation with a MIC>256 μg/ml for rifampin. Compounds of the current invention are potent against this highly rifampin-resistant strain with MICs in the 0.5 μg/ml level. Furthermore, compounds of the current invention demonstrated excellent activity against a quinolone-resistant strain S. aureus MT 1222 with MIC between 0.06-0.24 μg/ml, as compared to ciprofloxacin at 8 μg/ml.

The antibacterial activities of the compounds of the formula (I) are influenced by the chirality of the linker. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV (example 1), which has (R)-absolute configuration, is surprising more active than (S)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV (example 2), which has (S)-absolute configuration at the pro-chiral linker carbon marked by the asterisk (*).

TABLE 1

Antimicrobial activity (MIC, mcg/ml) of selected compounds

| Organism | | rifampin | ciprofloxacin | Example 1 | Example 2 |
|---|---|---|---|---|---|
| Staphylococcus aureua ATCC29213 | rifS | 0.008 | 0.25 | 0.06 | 0.24 |
| Staphylococcus aureus ATCC29213 rpoB$^{D417Y}$ | rifR | >256 | 0.25 | 0.5 | 8 |
| Staphylococcus aureus MT1222[a] gyrA$^{A116E}$ grlB$^{S80F}$ | cipR | 0.004 | 8 | 0.06 | 0.24 |
| Staphylococcus epidermidis ATCC12228 | rifS | 0.03 | 0.125 | 0.06 | 0.12 |
| Streptococcus pneumoniae ATCC6303 | rifS | 0.061 | 1 | 0.015 | 0.015 |
| Streptococcus pyogenes ATCC19615 | rifS | 0.013 | 0.5 | 0.015 | 0.03 |
| Haemophilus influenzae ATCC10211 | rifS | 0.24 | 0.008 | 0.5 | 0.5 |

[a]For strain MT1222 see: Ince & Hooper. Antimicrobial Agents and Chemotherapy, 2000, 44, 3344–50.

The compounds of the present invention can be used as medicaments, e.g. in the form of unit dosage pharmaceutical preparations for enteral or parenteral administration. For example, the compounds of formula I can be administered perorally, e.g. in the unit dosage forms of tablets, coated tablets, dragees, hard and soft gelatine capsules, solutions, emulsions or suspensions, rectally, e.g. in the form of suppositories, or parenterally, e.g. in the form of injection solutions.

The production of the pharmaceutical preparations can be done in a manner which will be familiar to any person skilled in the art by bringing the substances in accordance with the current invention, optionally in combination with other therapeutically valuable substances, into administration form together with or without suitable, non-toxic, inert, therapeutically compatible solid or liquid carrier materials and, if desired, the usual pharmaceutical adjuvants. The usual preservatives, solubilizers, stabilizers, wetting agents, emulsifiers, sweeteners, colorants, flavorants, salts for varying the osmotic pressure, buffers, masking agents and antioxidants such as ascorbic acid, sodium formaldehyde sulfoxylate come into consideration as pharmaceutical adjuvants. Both inorganic and organic carrier materials are suitable as such carrier materials. Thus, for example, lactose, corn starch or derivatives thereof, talc, stearic acid or its salts can be used as carrier materials for tablets, coated tablets, dragees and hard gelatine capsules. Suitable carriers for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

For parenteral administration the compounds of formula I and their salts are preferably provided as lyophilizates or dry powders for dilution with usual carriers such as water or isotonic saline. The usual preservatives, solubilizers, stabilizers, wetting agents, emulsifiers, colorants, salts for varying the osmotic pressure, buffers, masking agents and antioxidants such as ascorbic acid, sodium formadehye sulfoxylate can be considered as pharmaceutical adjuvants.

Thus, for example, a sterile lyophilizate can be prepared by wetting the compounds of formula I with ethanol, and mixing with 1M sodium carbonate solution or aqueous NaOH in amount to convert to their sodium salts. The solution is then added sodium formaldehyde sulfoxylate, frozen and lyophilized to provide a medicament.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections or infectious disease are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of formula I are distinguished by their ability to inhibit three bacterial enzymes, and therefore exbihit a high antibacterial activity and, respectively, may exhibit synergistic effects with the known antibacterials from other classes. Examples are the beta-lactam class, such as ceftriaxone; oxazolidinone class, such as linezolid; antibacterial peptides, such as vancomycin, dalbavancin, daptomycin; and polymycin B. They may exert synergistic effects with membrance-active polycationic peptide polymycins, such as colistin in the treatment of infections caused by Gram negative bacteria, such as, *E. coli, Pseudomonas aeruginosa*. Oral, rectal and parenteral administration comes into consideration in human medicine for such combinations of one or more compounds of the formula I in accordance with the invention. The combination ratio of compounds of the formula I to known antibiotics can vary within a wide range and can be fitted to the individual requirements in each particular case.

The total daily dose of the compounds of this invention administered to a human or animals in single or in divided doses can be in amounts, for example, from 0.1 to 100 mg/kg body weight or preferably from 0.25 to 25 mg/kg body weight. A daily dosage of about 10 mg to about 2 g of the present compounds can be administered into an average adult. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administrated orally, rectally, parenterally, intracisternally, intravaginally, intraperitoneally, topically, bucally, or as an oral or nasal spray.

Abbreviations

Abbreviations as used herein have the meanings known by one skilled in the art. Specifically, Ac represents acetyl group, AOC represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxylmethyl group, NMP represents N-methylpyrrolidinone, Ph represents phenyl group, Pr represents propyl group, TEA represents triethylamine, TFA represents trifluoroacetic acid, THF represents tetrahydrofuran, TMS, trimethylsilyl group, and Ts represents p-toluenesulfonyl group.

Specific Compositions

The compounds of the current invention may be better understood with reference to the following examples, which are representative of some of the embodiments of the invention, and are not intended to limit the invention.

All starting material used in these examples are either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra are recorded on a Varian 400 MHz magnetic resonance spectrometer. $^1$H NMR chemical shift are given in parts-per million ($\delta$) downfield from TMS using the residual solvent signal (CHCl$_3$=$\delta$ 7.27, CH$_3$OH=$\delta$ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant(s) (J) in hertz. The prefix app is occasionally applied in cases where the true signal multiplicity is unresolved and prefix br indicates a broad signal. Electrospray ionization mass spectra are recorded on a Finnegan LCQ advantage spectrometer.

EXAMPLE 1

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV

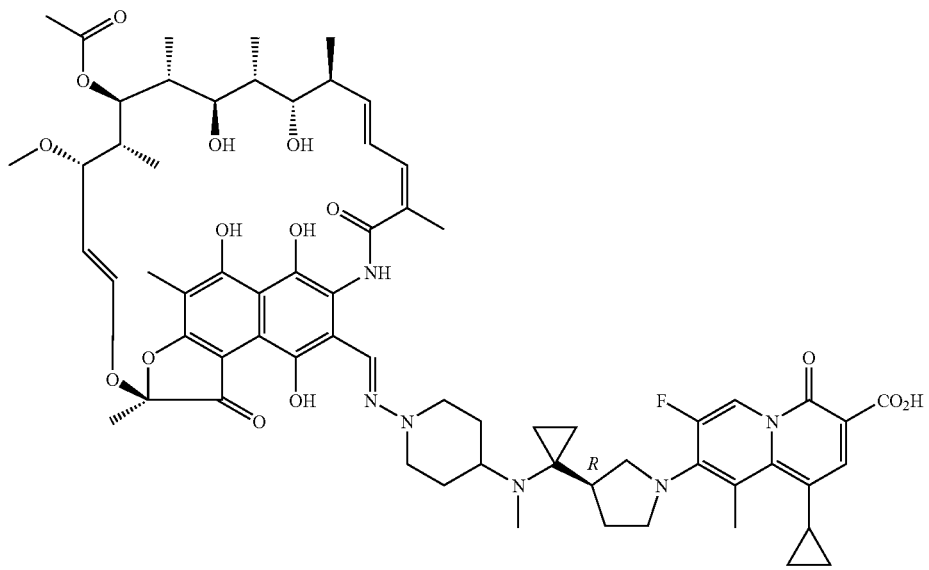

Step 1. (S)-Methanesulfonic acid 1-benzyl-pyrrolidin-3-yl ester

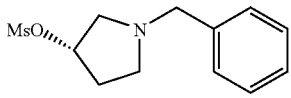

(S)-1-Benzyl-3-hydroxypyrrolidine (20.2 g, 114 mmol) was dissolved in toluene (200 mL). To this stirred solution, triethylamine (20 mL, 142 mmol) was added followed by methanesulfonyl chloride (10.5 mL, 136 mmol) during a period of 40 min at 0° C. The resultant slurry was allowed to stir for two hours at 0° C. and 7% sodium bicarbonate (200 mL) was added to the reaction mixture. Organic layer was separated, and the aqueous layer was extracted with toluene (3×100 mL). The combined organic layers were washed with saturated sodium bicarbonate (3×200 mL), dried over Na$_2$SO$_4$ and concentrated under reduced pressure to give (S)-methanesulfonic acid 1-benzyl-pyrrolidin-3-yl ester as a yellow oil (28 g, 96%). The material was used directly for next step without purification. $^1$H NMR (400 MHz, CDCl$_3$) δ 7.34-7.17 (m, 5H), 5.24-5.18 (m, 1H), 3.71 (d, J$_{AB}$=13.0 Hz, 1H), 3.64 (d, J$_{AB}$=13.0 Hz, 1H), 3.01 (s, 3H), 2.89-2.80 (m, 3H), 2.56-2.50 (m, 1H), 2.38-2.31 (m, 1H), 2.14-2.07 (m, 1H).

Step 2. (R)-1-benzyl-3-cyanopyrrolidine

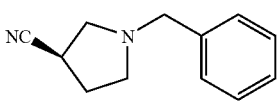

(S)-Methanesulfonic acid 1-benzyl-pyrrolidin-3-yl ester (28 g, 110 mmol) was dissolved in anhydrous acetonitrile (60 mL) and solid tetrabutylammonium cyanide (59 g, 220 mmol) was added at once at room temperature. The resulting mixture was heated at 65° C. for 16 h and cooled to room temperature. Saturated NaHCO$_3$ (100 mL) solution was added. The organic layer was separated and the aqueous layer extracted with toluene (3×100 mL). The combined organic layers were washed with water (3×100 mL), brine, and dried over Na$_2$SO$_4$ and concentrated under reduced pressure to give (R)-1-benzyl-3-cyanopyrrolidine as brown oil (21 g), which was vacuum distilled at 150° C./5 mmHg to give a colorless liquid (19 g, 85%): [α]$^{23}$–22.0° (c=2.5, MeOH); $^1$H NMR (400 MHz, CDCl$_3$) δ 7.36-7.17 (m, 5H), 3.66 (app s, 2H), 3.05-2.99 (m, 1H), 2.93 (app t, J=8.8 Hz, 1H), 2.72-2.60 (m, 3H), 2.31-2.22 (m, 1H), 2.17-2.11 (m, 1H).

Step 3. (R)-1-(1-Benzyl-pyrrolidin-3-yl)-cyclopropylamine

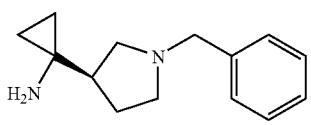

To a solution of (R)-1-benzyl-3-cyanopyrrolidine (10 g, 53.4 mmol) in anhydrous ether (200 mL) was added Ti(O-iPr)$_4$ (17.2 mL, 58.8 mmol) and the resulting solution was cooled to −78° C. EtMgBr (3.0 M in Et$_2$O, 35 mL, 105 mmol, Aldrich) was added drop-wise during a period of 40 min at −78° C. Anhydrous THF* (50 mL) was added to the resultant yellow suspension to facilitate stirring and the solution was stirred for 20 min at −78° C. The reaction mixture was allowed slowly to warm up to room temperature, then BF$_3$-Et$_2$O (13.4 mL, 107 mmol) was added and the resultant dark brown suspension was stirred at room temperature for 2 hrs. Both 1N HCl (100 mL) and Et$_2$O (200 mL) were introduced subsequently to the reaction mixture and stirring was kept for 20 min until both organic and aqueous phases became clear. It was basified using aqueous 20% NaOH (100 mL) and stirred for 30 min. The organic phase was separated and the aqueous phase was extracted with Et$_2$O (2×100 mL). The combined organic phase was dried over Na$_2$SO$_4$ and concentrated under reduced pressure to give (R)-1-(1-benzyl-pyrrolidin-3-yl)-cyclopropylamine as brown oil (10.5 g, 90%), which was vacuum distilled to give a colorless liquid (9 g, 77%). The product is sufficiently pure to use in next step. For characterization, a small amount of sample was purified by PTLC using solvent NH$_4$OH/MeOH/CH$_2$Cl$_2$ (1/60/340): $[\alpha]^{23}$ −10.0° (c=2.5, MeOH); $^1$H NMR (400 MHz, CDCl$_3$) δ 7.33-7.23 (m, 5H), 3.62 (d, $J_{AB}$=12.8 Hz, 1H), 3.56 (d, $J_{AB}$=12.8 Hz, 1H), 2.66-2.57 (m, 3H), 2.40-2.37 (m, 1H), 1.96-1.91 (m, 2H), 1.69-1.62 (m, 1H), 0.55-0.48 (m, 2H), 0.41-0.36 (m, 2H).

Step 4. (R)-4-{[1-(1-Benzyl-pyrrolidin-3-yl)-cyclopropyl]-methyl-amino}-piperidine-1-carboxylic acid tert-butyl ester

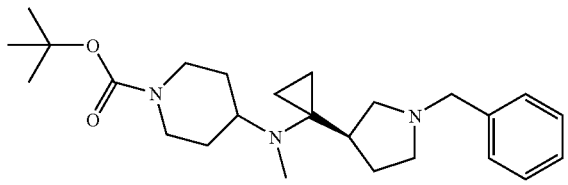

To a solution of (R)-1-(1-benzyl-pyrrolidin-3-yl)-cyclopropylamine (18.6 g, 87 mmol) and 4-oxo-piperidine-1-carboxylic acid tert-butyl ester (22.7 g, 113 mmol) in THF (500 mL) was added glacial HOAc (31 mL). The solution was stirred at room temperature for one hour and then NaBH(OAc)$_3$ (65 g, 306 mmol) was added. The resulted suspension was stirred at room temperature overnight before 37% aqueous solution of formaldehyde (30 mL, 262 mmol) was added. The reaction mixture was allowed to stir for 3 hrs and completed, then added aqueous 20% NaOH (300 mL) at 0° C. The mixture was allowed to stir for 2 h, and layers were separated. The aqueous layer was extracted with EtOAc (3×300 mL). The combined organic phase was dried over sodium sulfate, concentrated in vacuo. The residue was purified by flash chromatography (gradient eluation, 1% to 10% methanol in dichloromethane) to give the title compound as a pale yellow oil (27 g): ESI MS m/z 414.3 (M+H$^+$). $^1$H NMR (400 MHz, CDCl$_3$) δ 7.33-7.23 (m, 5H), 4.24-4.02 (m, 2H), 3.88-3.80 (m, 1H), 3.60 (d, $J_{AB}$=12.8 Hz, 1H), 3.53 (d, $J_{AB}$=12.8 Hz, 1H), 2.82-2.57 (m, 5H), 2.31 (s, 3H), 2.28-2.22 (m, 1H), 1.94-1.80 (m, 4H), 1.44 (s, 9H), 1.42-1.28 (m, 3H), 0.55-0.53 (m, 4H). The chiral purity of the product was analyzed by Chiral-Cel OD column (0.46 cm×25 cm, Daicel Chemical industries, Ltd, column catalog no. OD00CE-E1031) with acetonitrile in the presence of 0.1% diethylamine as mobile phase (flow rate 1 mL/min; retention time 5.23 min desired, 5.93 isomer) to be 95% ee.

Step 5. (R)-4-[Methyl-(1-pyrrolidin-3-yl-cyclopropyl)-amino]-piperidine-1-carboxylic acid tert-butyl ester

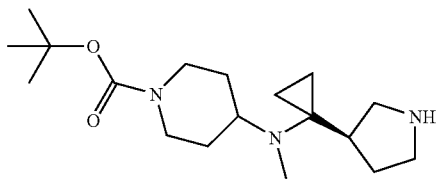

(R)-4-{[1-(1-benzyl-pyrrolidin-3-yl)-cyclopropyl]-methyl-amino}-piperidine-1-carboxylic acid tert-butyl ester (14 g) was dissolved in 150 mL glacial acetic acid at room temperature in a hydrogenation flask, air was evacuated, and filled with nitrogen. To this was added 30% Pd/C (5 g), flask was mounted to Parr shaker, nitrogen was evacuated and filled with hydrogen, and the mixture was shaken under hydrogen atmosphere at 60 psi in a Parr for 18 h. Reaction mixture was diluted with toluene (300 mL), filtered through a pad of celite. The filtrate was concentrated in vacuo, residue was digested in cold 30% NaOH at 0° C. and the product was extracted with ethyl acetate. The combined ethyl acetate solution was charged with 50 g of charcoal (Darco G-60), allowed to stir for 2 h, filtered, concentrated to give pale yellow oil, which can be vacuum distilled to give a clear oil (9.6 g). $^1$H NMR (400 MHz, CD$_3$OD) δ 4.04 (br s, 1H), 3.01 (dd, J=10.4 Hz and 7.6 Hz, 1H), 2.84 (dd, J=8.0 Hz and 5.2 Hz, 2H), 2.64-2.55 (m, 3H), 2.48-2.43 (m, 2H), 2.30 (s, 3H), 2.28-2.23 (m, 1H), 2.23-1.74 (m, 3H), 1.40 (s, 9H), 1.35-1.28 (m, 2H), 1.18-1.12 (m, 2H), 0.53-0.45 (m, 4H).

Step 6. 8-(3-{1-[(1-tert-Butoxycarbonyl-piperidin-4-yl)-methyl-amino]-cyclopropyl}-pyrrolidin-1-yl)-1-cyclopropyl-7-fluoro-9-methyl-4-oxo-4H-quinolizine-3-carboxylic acid ethyl ester

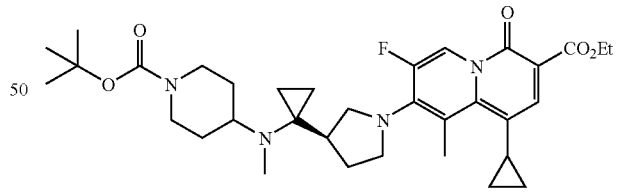

A stirred solution of ethyl 8-chloro-1-cyclopropyl-7-fluoro-9-methyl-4-oxo-4H-quinolizinone-3-carboxylate (8.4 g, 25 mmol) and 4-[methyl-(1-pyrrolidin-3-yl-cyclopropyl)-amino]-piperidine-1-carboxylic acid tert-butyl ester (10.6 g, 25 mmol) in the presence of sodium bicarbonate (8 g) in acetonitrile (150 mL) in a round bottom flask was heated under reflux for 5 hours. The solvent was removed in vacuo, residue was partitioned into 1N NaOH and ethyl acetate and well-shaken. The organic layer was separated, washed with brine, dried over sodium sulfate and concentrated in vacuo. The residue was purified by flash chromatography (75% ethyl acetate in hexane, then 10% MeOH in dichloromethane) to give a yellow solid (15 g, 99%). ESI MS m/z 611.3 (M+H$^+$). $^1$H NMR (400 MHz, CDCl$_3$) δ 9.25 (d, J=10.8 Hz, 1H), 8.18 (s, 1H), 4.42-4.37 (m, 2H), 4.15-4.10 (m, 3H), 3.92-3.88 (m, 1H), 3.58-3.56 (m, 2H), 3.48-3.44 (m, 1H), 2.73-2.62 (m, 5H), 2.57 (s, 3H), 2.39 (s, 3H), 2.18-2.13 (m, 1H), 2.00-1.94 (m, 1H), 1.84-1.78 (m, 2H), 1.46 (s, 9H), 1.42 (t, J=7.2 Hz, 3H), 1.28-1.25 (m, 1H), 1.07-0.93 (m, 2H), 0.84-0.68 (m, 4H), 0.60-0.52 (m, 2H).

Step 7. 8-(3-{1-[(1-tert-Butoxycarbonyl-piperidin-4-yl)-methyl-amino]-cyclopropyl}-pyrrolidin-1-yl)-1-cyclopropyl-7-fluoro-9-methyl-4-oxo-4H-quinolizine-3-carboxylic acid

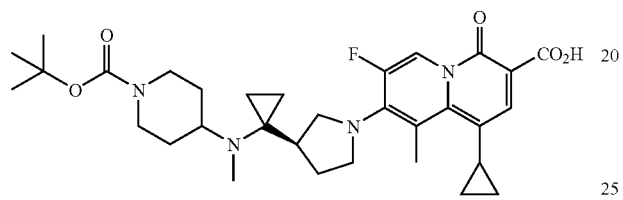

To a solution of 8-(3-{1-[(1-tert-butoxycarbonyl-piperidin-4-yl)-methyl-amino]-cyclopropyl}-pyrrolidin-1-yl)-1-cyclopropyl-7-fluoro-9-methyl-4-oxo-4H-quinolizine-3-carboxylic acid ethyl ester (15 g, 24 mmol) in ethanol (200 mL) was added the solution of LiOH (10 g, 238 mmol) in water (100 mL) in a round bottom flask. The solution was heated at 60° C. for one hour. The resulting solution was partitioned between dichloromethane (400 mL) and saturated aqueous NH$_4$Cl (200 mL) and well shaken. The organic layer was separated, washed with brine, dried over sodium sulfate and concentrated in vacuo to yield a yellow solid (14 g). This was used without further purification.

Step 8. 1-Cyclopropyl-7-fluoro-9-methyl-8-{3-[1-(methyl-piperidin-4-yl-amino)-cyclopropyl]-pyrrolidin-1-yl}-4-oxo-4H-quinolizine-3-carboxylic acid

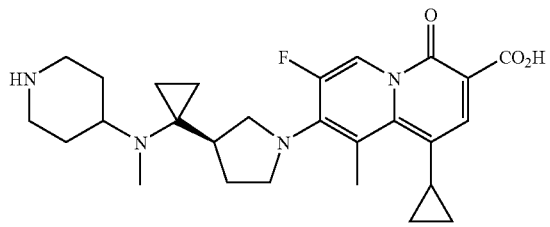

To a stirred solution of 8-(3-{1-[(1-tert-butoxycarbonyl-piperidin-4-yl)-methyl-amino]-cyclopropyl}-pyrrolidin-1-yl)-1-cyclopropyl-7-fluoro-9-methyl-4-oxo-4H-quinolizine-3-carboxylic acid (14 g) in dichloroethane (100 mL) was added trifluoroacetic acid (30 mL) at 0° C. slowly. The resulting solution was stirred at 0° C. to room temperature for one hour. The solvent was removed in vacuo to yield yellow oil, which was dissolved in 20% IPA in dichloromethane and the solution was neutralized by sat. aq NaHCO$_3$ resulting two clear phases, and the two phases were well shaken. The organic layer was separated, and the aqueous phase was extracted with 20% IPA/CH$_2$Cl$_2$. The combined organic extracts were washed with brine, dried over sodium sulfate and concentrated in vacuo to give yellow solid (10 g), the solid was crystallized from methanol/water to give crystalline solid (8 g). ESI MS m/z 483.3 (M+H$^+$). $^1$H NMR (400 MHz, CD$_3$OD) δ 8.88 (d, J=10.0 Hz, 1H), 7.93 (s, 1H), 4.03-3.98 (m, 1H), 3.79-3.75 (m, 1H), 3.66-3.62 (m, 1H), 3.58-3.52(m, 1H), 3.47-3.44 (m, 2H), 3.05-2.88 (m, 4H), 2.62 (s, 3H), 2.49 (s, 3H), 2.35-2.23 (m, 3H), 2.06-2.02 (m, 1H), 1.70-1.58 (m, 2H), 1.51-1.44 (m, 1H), 0.93-0.64 (m, 8H).

Step 9. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV 1-Cyclopropyl-7-fluoro-9-methyl-8-{3-[1-(methyl-piperidin-4-yl-amino)-cyclopropyl]-pyrrolidin-1-yl}-4-oxo-4H-quinolizine-3-carboxylic acid (9.2 g, 19 mmol) was dissolved in 1 N NaOH solution (120 mL) at room temperature. This was cooled to 0° C. and under argon atmosphere. To this homogenous solution was added a freshly-prepared solution of hydroxylamine-O-sulfuric acid (H$_2$N—OSO$_3$H, 2 g, 18.5 mmol) in H$_2$O (10 mL) dropwise at 0° C. The resultant solution was stirred at this temperature for 1 h, excess acetic acid (22 mL) was added to acidify to pH 5, followed by ascorbic acid (1 g). The solution was then diluted with methanol (280 mL). To the stirred resultant solution at room temperature, was added a homogeneous solution of 3-formylrifamycin (8.2 g, 11.3 mmol in 40 mL of methanol/THF (3:1) slowly in 30 min. The product slowly precipitates out of homogenous reaction mixture. After addition, the stirred reaction mixture was kept for 30 min at room temperature and cooled to 0° C. for 1 h, and precipitate was collected, and washed with cold methanol (3×20 mL) to give 9.5 g. The collected precipitate was dissolved in dichloromethane (100 mL), this solution was stirred with 5% citric acid solution (100 mL) in the presence of 0.5% ascorbic acid for two hours and the two phases were shaken. Organic phase was separated, washed with the same aqueous solution, dried over sodium sulfate. To the dried filtrate, added half the volume of ethanol and concentrated in vacuo to give an orange solid (8.5 g). One gram of the orange solid was crystallized as follows: The solid (1 gram) was dissolved in 5 mL of acetone and water (95:5), the stirred solution was heated on an oil-bath at 55-60° C. until homogeneous. The solution was slowly cooled with stirring (200 rpm) to room temperature. Once precipitate forms, the mixture was allowed to stir at room temperature for 2 h, and cooled to 0° C. on ice-bath for 2 h, before collecting the precipitate using a buchner funnel with aid of cold solvent. The cake was pressed-dry, and washed with 5 mL cold acetone/water (95:5) and pressed-dry again. The cake was vacuum dried to a constant weight (830 mg obtained) to produce the title compound. $^1$H NMR (400 MHz, CDCl$_3$) δ 13.82 (s, 1H), 13.52 (br s, 1H), 13.25 (singlet, 1H), 11.98 (singlet, 1H), 9.04 (d, J=9.2 Hz, 1H), 8.22 (s 1H), 7.97 (s, 1H), 6.58-6.50 (m, 1H), 6.37-6.34 (m, 1H), 6.18 (d, J=12.4 Hz, 1H), 5.94-5.87 (m, 1H), 5.07 (dd, J=6.8, 12.8 Hz, 1H), 4.89 (d, J=10.8 Hz, 1H), 3.93-3.87 (m, 1H), 3.72 (d, J=9.6 Hz, 1H), 3.66-3.52 (m, 4H), 3.48-3.42 (m, 3H), 3.00 (s, 3H), 3.00-2.95 (m, 1H), 2.65-2.50 (m, 6H), 2.37 (s, 3H), 2.36-2.30 (m, 1H), 2.19 (s, 3H), 2.18-2.10 (m, 1H), 2.02 (app s, 6H), 2.00-1.82 (m, 2H), 1.76 (s, 3H), 1.65-1.40 (m, ~10H), 1.32-1.17 (m, 2H), 1.08-1.02 (m, 1H), 0.96 (d, J=6.8 Hz, 3H), 0.90-0.85 (m, 1H), 0.82 (d, J=6.8 Hz, 3H), 0.78-0.62 (m, 3H), 0.56 (d, J=6.4 Hz, 3H), −0.35 (d, J=6.8 Hz, 3H); MS: ESI m/z 1173.6 (M−MeO, most abundant)$^+$, 1205.6 (M+H, parent)$^+$; HPLC analysis: retention time: 17.8 min isocratic elution: 47% B in 30 min (analytical column: Agilent, Zorbax SB-aq, 5 mc-m, 4.6×150 mm; solvent A: HPLC water in the presence of 0.1% TFA; solvent B: HPLC acetonitrile in the presence of 0.1% TFA).

EXAMPLE 2

(S)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV

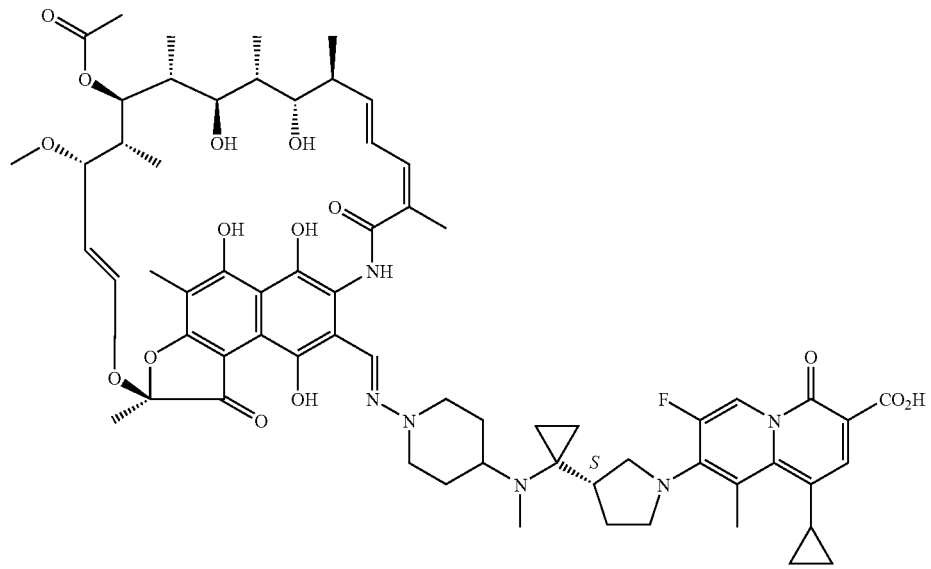

The title compound was prepared by following the same scheme as the preparation of (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV, except (R)-1-benzyl-3-hydroxypyrrolidine was used in the place of (S)-1-benzyl-3-hydroxypyrrolidine in the step 1 of example 1. HPLC analysis: retention time: 20.5 min isocratic elution: 47% B in 30 min (analytical column: Agilent, Zorbax SB-aq, 5 mc-m, 4.6×150 mm; solvent A: HPLC water in the presence of 0.1% TFA; solvent B: HPLC acetonitrile in the presence of 0.1% TFA).

EXAMPLE 3

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin S

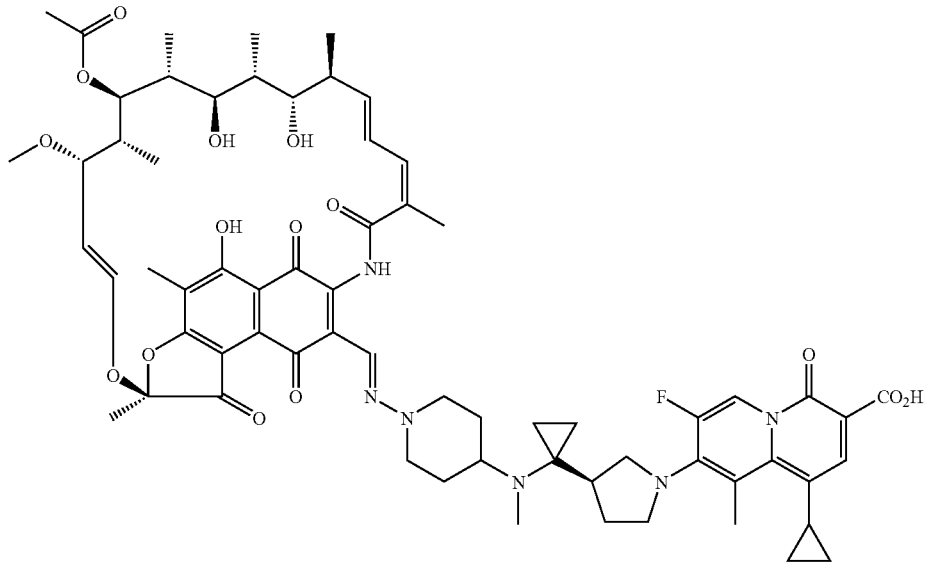

To a solution of (R)-3-[(4-{1-{1-(3-carboxy-1-cyclopropyl-7-fluoro-9-methyl-4-oxo-4H-quinolizine-9-yl)-pyrrolidin-3-yl-cyclopropyl]-methylamino}-piperidin-1-ylimino)-methylenyl]-rifamycin SV (250 mg, 0.207 mmol) in ethyl acetate (50 ml) was added a solution of potassium hexacyanoferrate (III) (500 mg, 1.52 mmol) dissolved in pH 7.4 aqueous phosphate buffer (50 ml). The mixture was stirred vigorously at 23° C. for 1 h then an additional portion of potassium hexacyanoferrate (III) (500 mg, 1.52 mmol) was added and stirring was continued for 1 hr. The organic layer was separated, dried over anhydrous sodium sulfate and concentrated to give the product as dark oil. The oil was dissolved in dichloromethane, diluted with hexanes and slowly concentrated to give the product as a dark, fine powder, 177 mg (71%). ESI MS m/z 1171 (M−MeO most abundant), 1203.3 (M+H⁺); HPLC analysis: retention time: 14.45 min isocratic elution: 47% B in 30 min (analytical column: Agilent, Zorbax SB-aq, 5 μm, 4.6×150 mm; solvent A: HPLC water in the presence of 0.1% TFA; solvent B: HPLC acetonitrile in the presence of 0.1% TFA); $^1$H NMR (400 MHz, CDCl$_3$) δ 13.72 (br s, 1H), 12.63 (s, 1H), 10.4-10.2 (m, 2H), 8.98-8.92 (m, 1H), 8.10 (s, 1H), 7.60 (s, 1H), 6.8-6.6 (m, 2H), 6.30-6.20 (m, 1H), 6.09-5.95 (m, 1H), 5.95-5.80 (m, 1H), 5.05-4.84 (m, 2H), 3.95-3.20 (m, 8H), 2.95 (s, 3H), 2.82-2.62 (m, 7H), 2.60-2.40 (m, 1H), 2.42 (s, 3H), 2.25 (s, 3H), 2.20-2.15 (s, 3H), 1.91 (s, 3H), 2.05-1.72 (m, 6H), 1.72-1.20 (m, 18H), 1.09-1.00 (s, 3H), 0.99-0.40 (m, 4H), 0.1-0.1 (s, 3H).

EXAMPLE 4

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-25-deacetyl-rifamycin SV

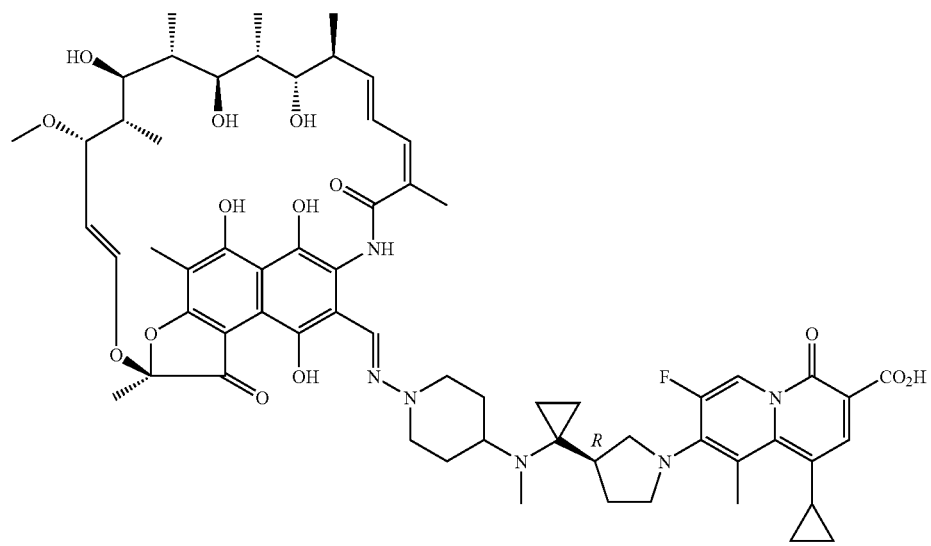

To a solution of (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin S (267 mg, 0.22 mmol) prepared as indicated above in MeOH (5.0 mL) and THF (5.0 mL) was added a solution of LiOH.H$_2$O (37.0 mg, 0.88 mL) in H$_2$O (2.0 mL) at 0° C. The resultant solution was stirred at the same temperature for about 5 hours, diluted with CH$_2$Cl$_2$, washed with 5% AcOH/H$_2$O solution twice and dried over Na$_2$SO$_4$. The solvent was removed and residue was purified by preparative thin layer chromatography with 10% MeOH/CH$_2$Cl$_2$ to give a dark brown solid. The solid was taken up in MeOH (10 mL) and to which a solution of ascorbic acid (100 mg, 0.57 mmol) in H$_2$O (2.0 mL) was added. The mixture was stirred at room temperature for 2 hours, diluted with CH$_2$Cl$_2$, washed with H$_2$O three times and dried over Na$_2$SO$_4$. The sovent was removed to produce the title compound as an orange solid (136 mg, 53% yield). ESI MS m/z 1131.5 (M−MeO)$^+$; $^1$H NMR (400 MHz, CDCl$_3$) δ 13.87 (s, 1H), 13.53 (br s, 1H), 13.34 (s, 1H), 13.24 (s, 1H), 12.12 (s, 1H), 9.02 (d, J=9.2 Hz, 1H), 8.27 (s 1H), 8.16 (s, 1H), 6.81-6.72 (m, 1H), 6.43 (d, J=12.8 Hz, 1H), 6.23 (d, J=12.8 Hz, 1H), 5.88-5.81 (m, 1H), 5.21 (dd, J=6.8, 12.8 Hz, 1H), 4.82 (br s, 1H), 3.98-3.90 (m, 2H), 3.75-3.50 (m, 8H), 3.39 (d, J=12.0 Hz, 3H), 3.24 (s, 3H), 3.23-3.20 (m, 1H), 3.20 (br s, 1H), 2.74-2.52 (m, 6H), 2.44 (s, 3H), 2.38-2.30 (m, 2H), 2.23 (s, 3H), 2.18 (s, 1H), 2.08 (s, 3H), 2.07-1.90 (m, 4H), 1.80 (s, 3H), 1.66-1.50 (m, 2H), 1.12-1.07 (m, 1H), 1.03 (d, J=7.2 Hz, 3H), 1.02-0.95 (m, 1H), 0.92-0.78 (m, 5H), 0.76-0.60 (m, 7H), 0.47 (d, J=6.8 Hz, 3H); HPLC analysis: retention time: 9.3 min isocratic elution: 47% B in 30 min (analytical column: Agilent, Zorbax SB-aq, 5 μm, 4.6×150 mm; solvent A: HPLC water in the presence of 0.1% TFA; solvent B: HPLC acetonitrile in the presence of 0.1% TFA).

EXAMPLE 5

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-amino}-piperidin-1-ylimino)-methylenyl]-rifamycin SV The title compound was prepared by following the same scheme as the preparation of (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV (example 1), except formaldehyde was not added in the step 4 of the preparation of example 1. ESI MS m/z 1159.6 (M-MeO)$^+$; $^1$H NMR (400 MHz, CDCl$_3$) δ 13.88 (s, 1H), 13.51 (br s, 1H), 13.28 (s, 1H), 13.04 (br s, 1H), 12.01 (s, 1H), 9.03 (d, J=10.8 Hz, 1H), 8.26 (s 1H), 8.18 (s, 1H), 6.62-6.55 (m, 1H), 6.41 (d, J=11.2 Hz, 1H), 6.23 (d, J=12.4 Hz, 1H), 5.95 (d, J=16.4 Hz, 1H), 5.11 (dd, J=6.8, 12.0 Hz, 1H), 4.93 (d, J=10.8 Hz, 1H), 3.97 (br s, 1H), 3.76 (d, J=9.2 Hz, 1H), 3.66-3.46 (m, 8H), 3.05 (s, 3H), 3.04-2.92 (m, 2H), 2.84-2.64 (m, 3H), 2.62 (s, 6H), 2.41-2.37 (m, 1H), 2.23 (s, 3H), 2.19-2.15 (m, 1H), 2.07 (app s, 6H), 2.04-1.96(m, 4H), 1.87-1.82 (m, 1H), 1.81 (s, 3H), 1.70-1.36 (m, 4H), 1.12-1.07 (m, 1H), 1.01 (d, J=6.4 Hz, 3H), 1.00-0.92 (m, 1H), 0.86 (d, J=6.4 Hz, 3H), 0.71-0.52 (m, 7H), −0.31 (d, J=6.4 Hz, 3H).

EXAMPLE 6

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV, disodium (a medicament)

(R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV (115 mg, 0.095 mmol) was placed in a round bottom flask, to this was added ethanol (0.2 mL) at room temperature and mixed well, 0.22 mL of 1M sodium carbonate solution added, the mixture was allowed to stir for 5

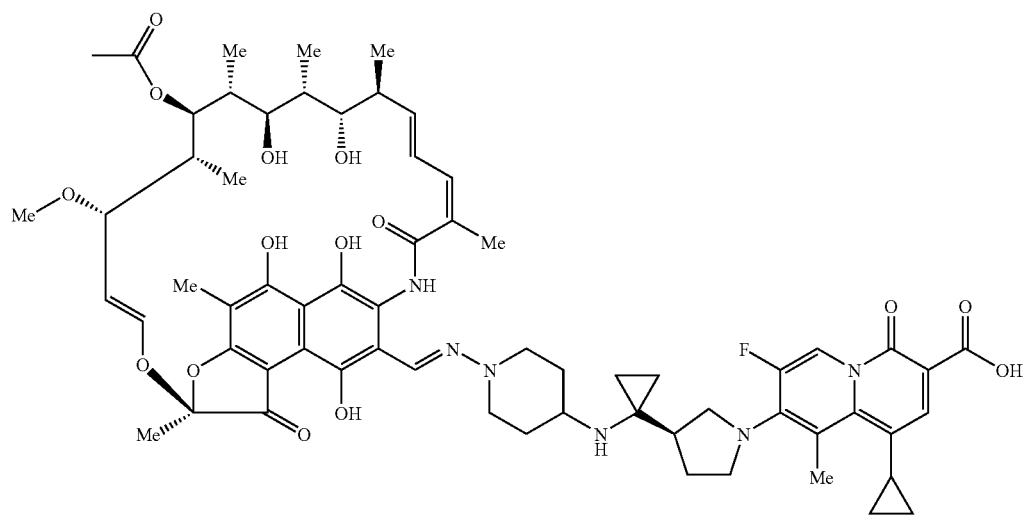

min, and diluted with 4.5 mL of water and allowed to stir for 30 min or until homogeneous, sodium formaldehyde sulfoxylate (HOCH$_2$SO$_2$Na.2H$_2$O) (1.2 mg) was added, and stirred for 5 min, and homogeneous solution was filtered. The filtrate placed in dry ice-acetone bath under nitrogen for 30 min. The frozen solid was lyophilized to give a fluffy orange solid (137 mg, 82.7% drug potency).

EXAMPLE 7

Lyophilization

A compound of formula I, e.g. (R)-3-[(4-{1-[1-(3-carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV was lyophilized by mixing with the components shown below in Table 7.1.

TABLE 7.1

|  | Weight |
| --- | --- |
| Compound of formula I | 120 mg |
| Sodium hydroxide | 8 mg |
| Sodium formaldehyde sulfoxylate | 1.2 mg |
| Total weight | 122 mg |

The mixture of components was then frozen and lyophilized.

One skilled in the art readily appreciates that the disclosed invention is well adapted to carry out the mentioned and inherent objectives. Examples, pharmaceutical compositions, medicaments, methods, procedures and techniques described herein are presented as representative of the preferred embodiments and are not intended as limitations of the scope of the invention. Thus, other uses will occur to those skilled in the art that are encompassed within the spirit and scope of the described invention.

What is claimed is:
1. A compound of structural formula I:

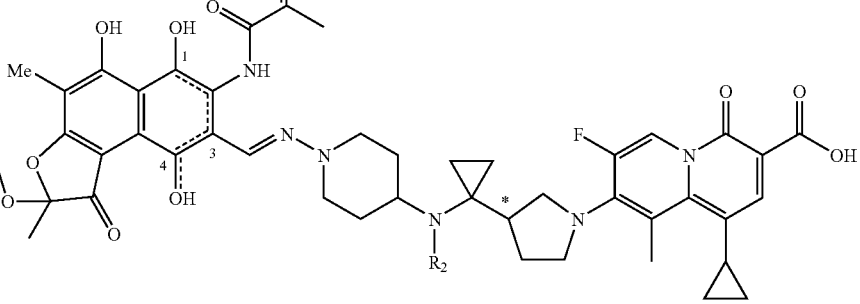

I or pharmaceutically acceptable salts of the structural formula I, wherein:

R₁ is hydrogen or acetyl;

R₂ is hydrogen, or alkyl having from one to six carbon atoms;

wherein asterik (*) denotes the carbon bearing the chiral center, wherein absolute configuration is assigned as R or S.

2. A compound having a formula selected from the group consisting of:

a. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV:

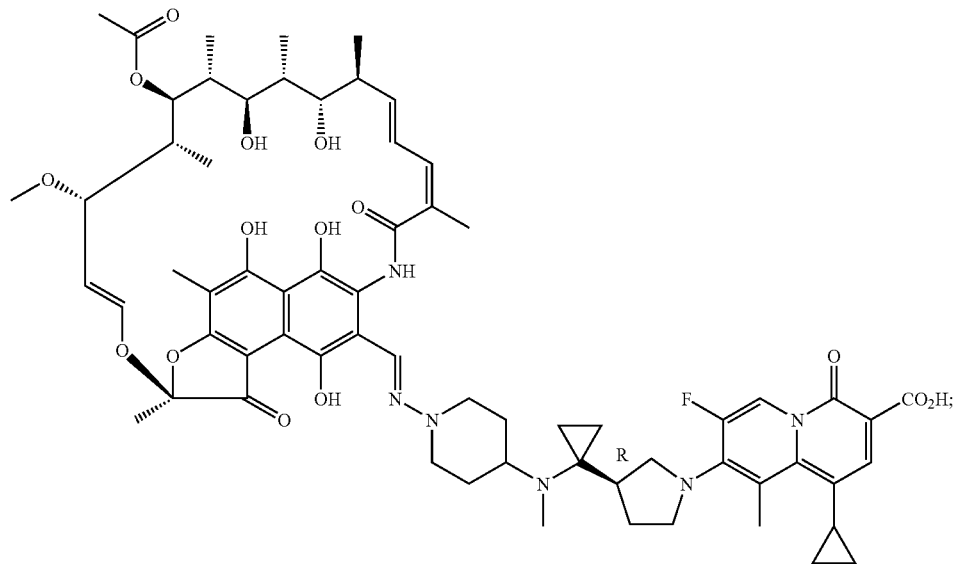

b. (S)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV:

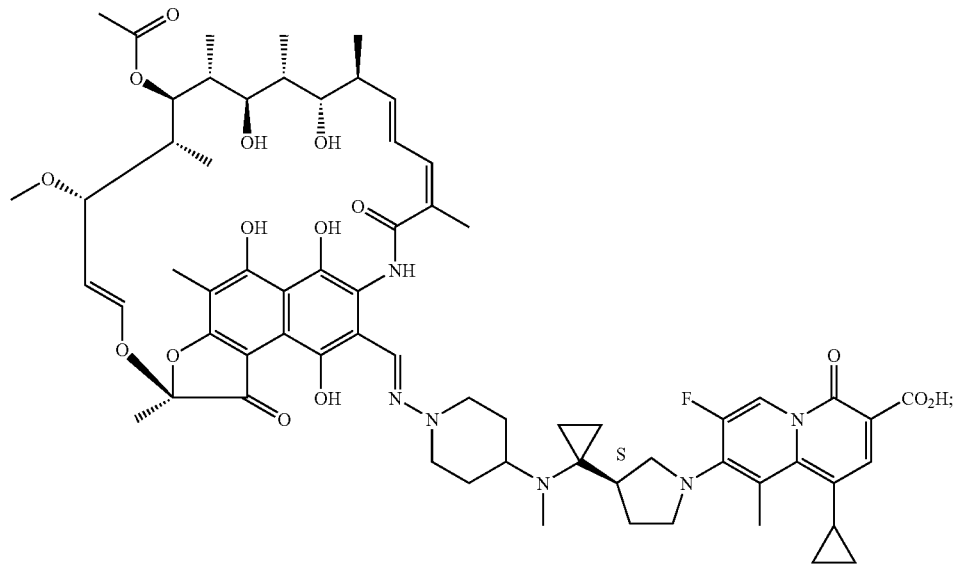

c. (R/S)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV:
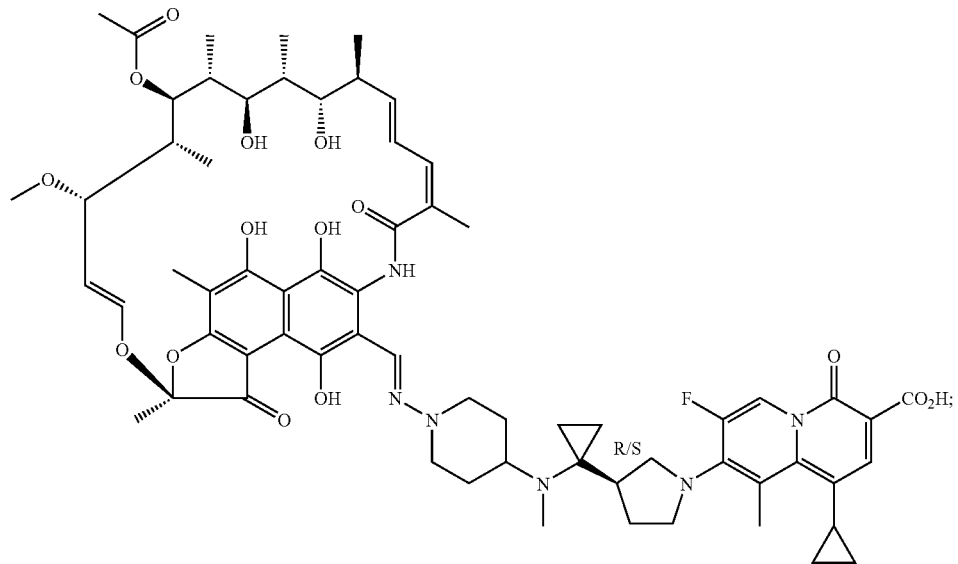
d. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin S:
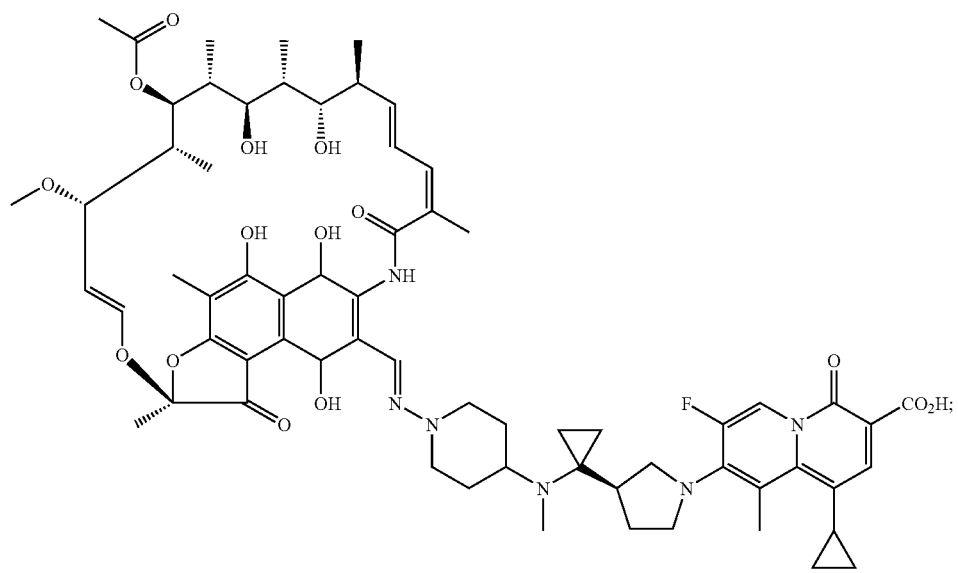

e. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-25-deacetyl-rifamycin SV:
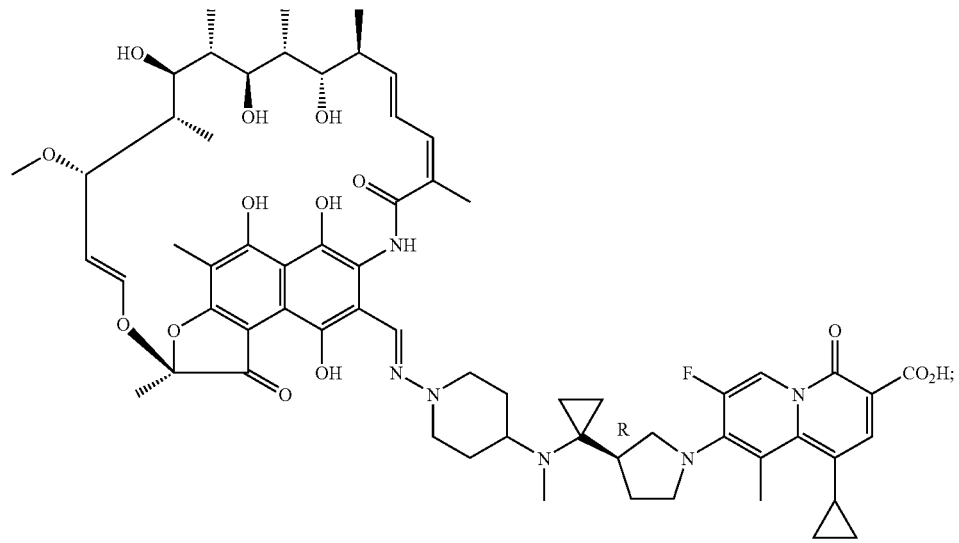
f. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-amino}-piperidin-1-ylimino)-methylenyl]-rifamycin SV:
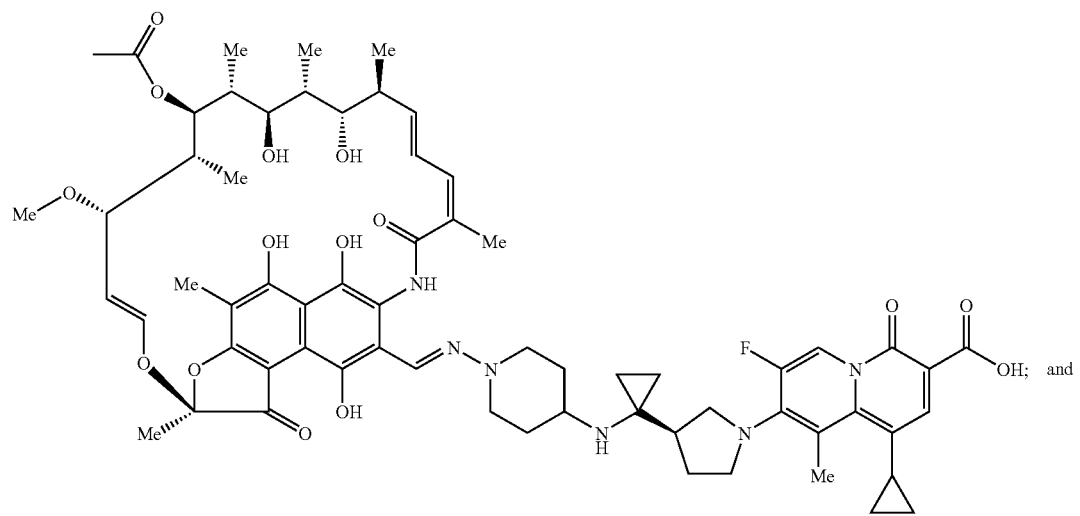
and g. (R)-3-[(4-{1-[1-(3-Carboxy-1-cyclopropyl-7-fluoro-9-methyl-4-oxo-4H-quinolizine-8-yl)-pyrrolidin-3-yl-cyclopropyl]-methylamino}-piperidin-1-ylimino)-methylenyl]-rifamycin SV:
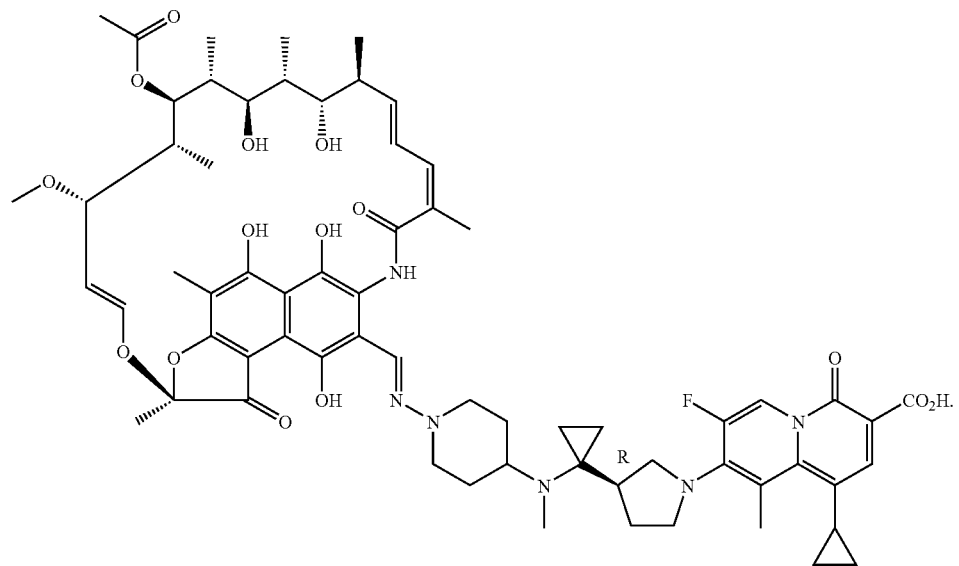
3. A method of preparing a compound of structural formula I:
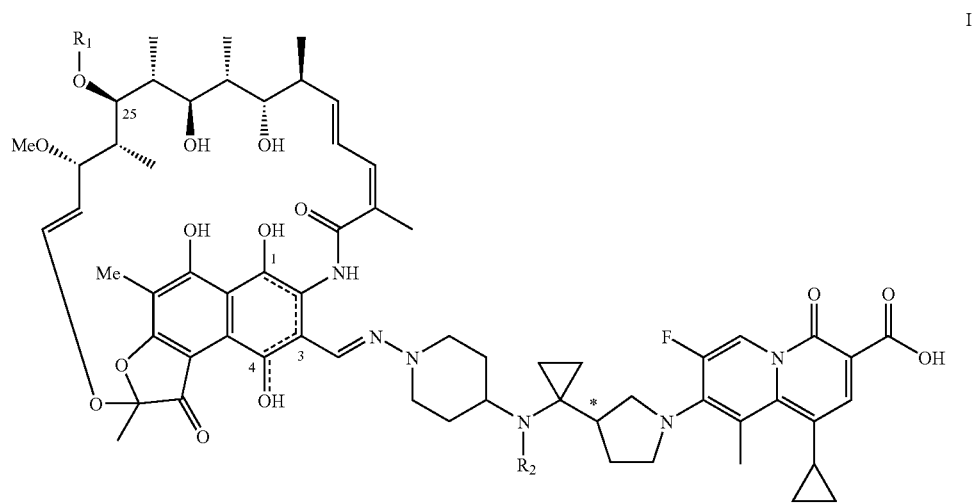

or pharmaceutically acceptable salts of the structural formula I,
wherein:
$R_1$ is hydrogen or acetyl;
$R_2$ is hydrogen, or alkyl having from one to six carbon atoms;
wherein asterik (*) denotes the carbon bearing the chiral center, wherein absolute configuration is assigned as R or S,
comprising:
coupling a hydrazine of formula AF2:

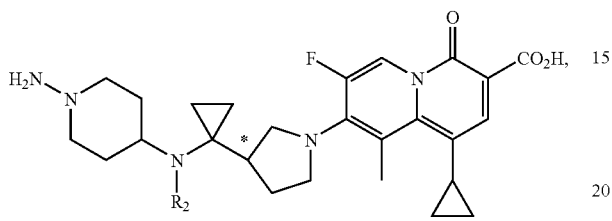

AF2 to 3-formylrifamycin of formula 3FRF:

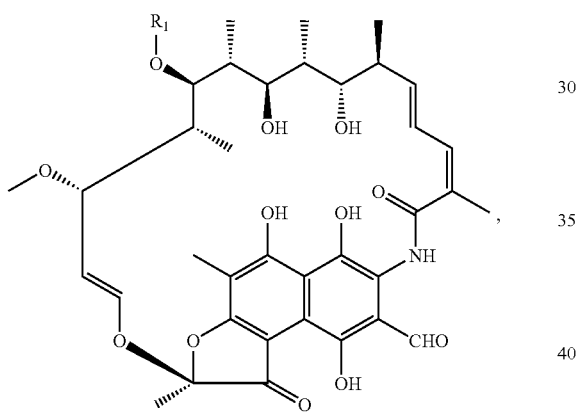

3FRF in a solvent at a temperature ranging from about 0° C. to about 50° C.

4. The method of claim 3, wherein the solvent is water, ethanol, methanol, THF, acetone, acetic acid, or a mixture thereof.

5. The method of claim 3, further comprising adding an additive selected from the group consisting of sodium hydroxide, ascorbic acid, a salt of ascorbic acid, and sodium acetate.

6. A method of preparing a diaminoacid of formula AF1:

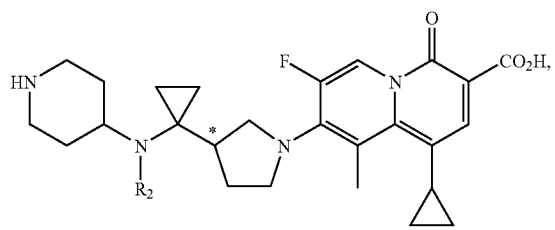

AF1 comprising:

reacting a triamine of formula BF1:

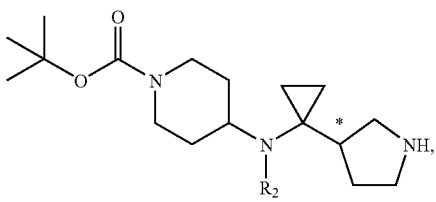

BF1 with a 4H-4-oxoquinolizine of formula BF2:

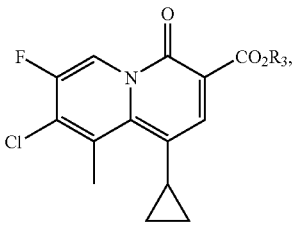

BF2 in a solvent in the presence of a first base at a temperature ranging from about 20° C. to about 100° C. to produce a compound of formula BF3:

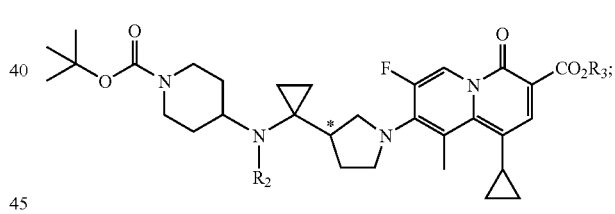

BF3 adding a second base in an alcoholic solvent to the compound of formula BF3 to produce a compound of formula BF4:

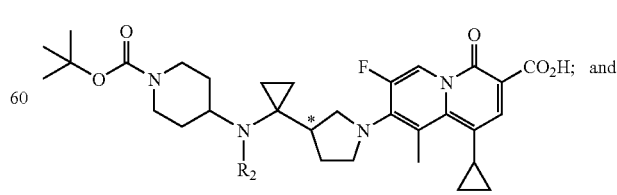

BF4 adding an acid to the compound of formula BF4 to produce the diaminoacid of formula AF 1.

7. The method of claim 6, wherein the solvent is acetonitrile, the first base is NaHCO₃, the second base is LiOH, the alcoholic solvent is ethanol, and the acid is trifluoroacetic acid.

8. A method of preparing a protected triamine of formula BF1:

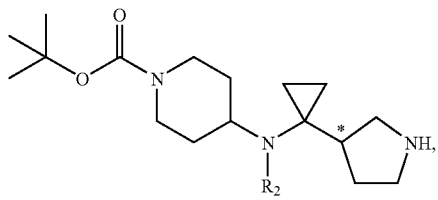

comprising:

reacting 1-benzyl-3-hydroxypyrrolidine with a mesylating agent in the presence of a base and in a first solvent to produce a mesylate;

reacting the mesylate with a cyanide in the presence of a phase transfer catalyst in a second solvent at a temperature ranging from about 20° C. to about 70° C. to produce a cyano compound;

reacting the cyano compound with ethylmagnesium bromide in the presence of titanium tetra-isopropoxide to produce an intermediate cyano compound;

reacting the intermediate cyano compound with a Lewis acid in a third solvent at a temperature ranging from about −78° C. to about room temperature to produce a cyclopropylamine;

reacting the cyclopropylamine with N—BOC 4-piperidone to produce an intermediate aminated cyclopropylamine;

reacting the intermediate animated cyclopropylamine with reductive hydride in a fourth solvent to produce a compound of formula CF1:

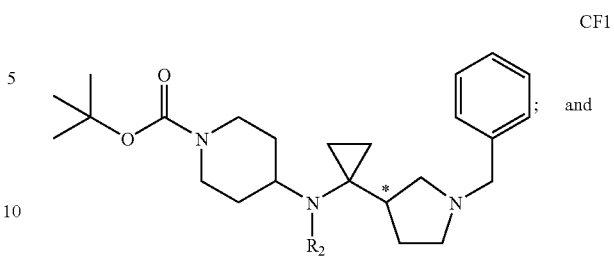

reacting the compound of formula CF1 with a palladium catalyst in a fifth solvent to produce the protected triamine.

9. The method of claim 8, wherein the mesylating agent is mesyl chloride or mesyl anhydride, the base is triethylamine, and the first solvent is toluene or ethyl acetate.

10. The method of claim 8, wherein the cyanide is tetrabutylammonium cyanide, triethylbenzylammonium cyanide, or mineral cyanide, wherein the phase transfer catalyst is tetrabutylammonium cyanide, and wherein the second solvent is acetonitrile.

11. The method of claim 8, wherein the Lewis acid is BF₃ etherate and the third solvent is THF, ether, dioxane, or a mixture thereof.

12. The method of claim 8, wherein the reductive hydride is sodium triacetoxyborohydride and the fourth solvent is THF, dichloromethane, acetic acid, or a mixture thereof.

13. The method of claim 8, wherein the palladium catalyst is 10% palladium on charcoal or 20% palladium hydroxide, and wherein the fifth solvent is ethanol, methanol, acetic acid, or a mixture thereof.

14. A phamaceutical composition, useful as a medicament for treatment or prevention of bacterial infections, comprising therapeutically effective amount of a compound in accordance with claim 1 in combination with a pharmaceutically acceptable carrier.

15. A method of treating or preventing bacterial infections in a patient comprising administering a pharmaceutical composition as defined in claim 14.

* * * * *

UNITED STATES PATENT AND TRADEMARK OFFICE
CERTIFICATE OF CORRECTION

PATENT NO. : 7,226,931 B2
APPLICATION NO. : 11/186425
DATED : June 5, 2007
INVENTOR(S) : Ding et al.

It is certified that error appears in the above-identified patent and that said Letters Patent is hereby corrected as shown below:

In the Abstract, first page, right-hand column, section 57, the structure "I" should appear as follows:

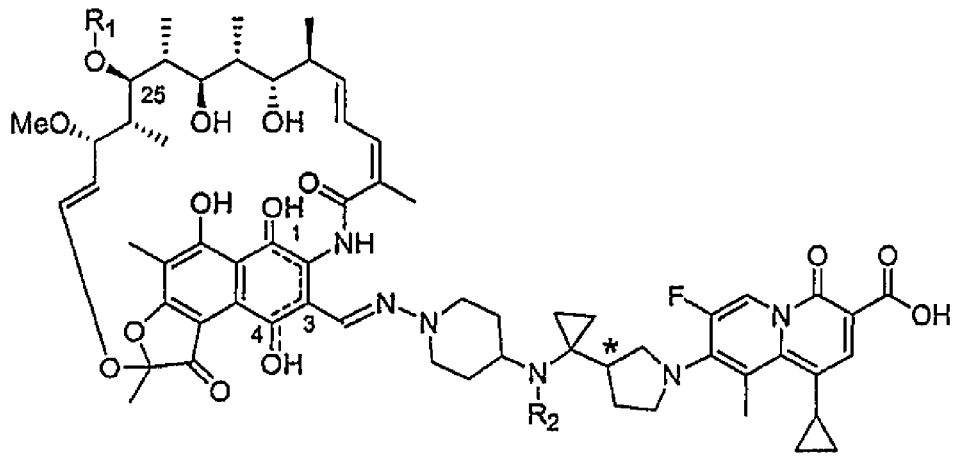

In Column 2, line 12, the structure "I" should appear as follows:

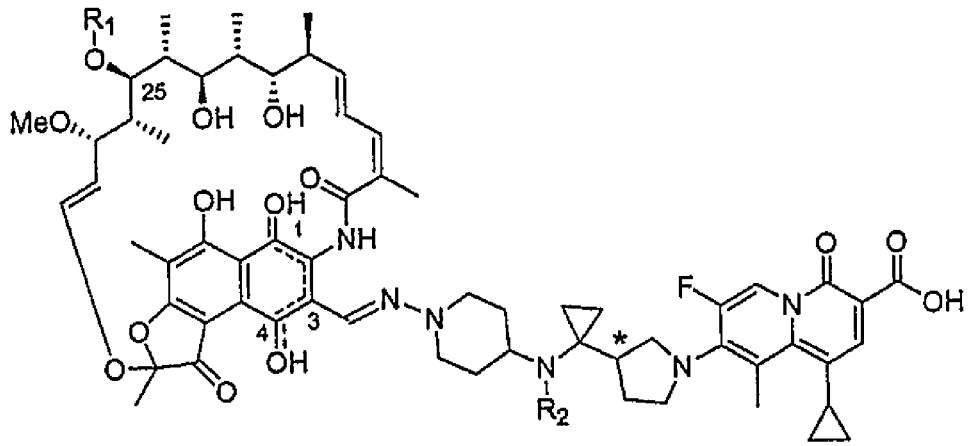

UNITED STATES PATENT AND TRADEMARK OFFICE
CERTIFICATE OF CORRECTION

PATENT NO. : 7,226,931 B2
APPLICATION NO. : 11/186425
DATED : June 5, 2007
INVENTOR(S) : Ding et al.

It is certified that error appears in the above-identified patent and that said Letters Patent is hereby corrected as shown below:

In Column 3, line 10, the structure "I" should appear as follows:

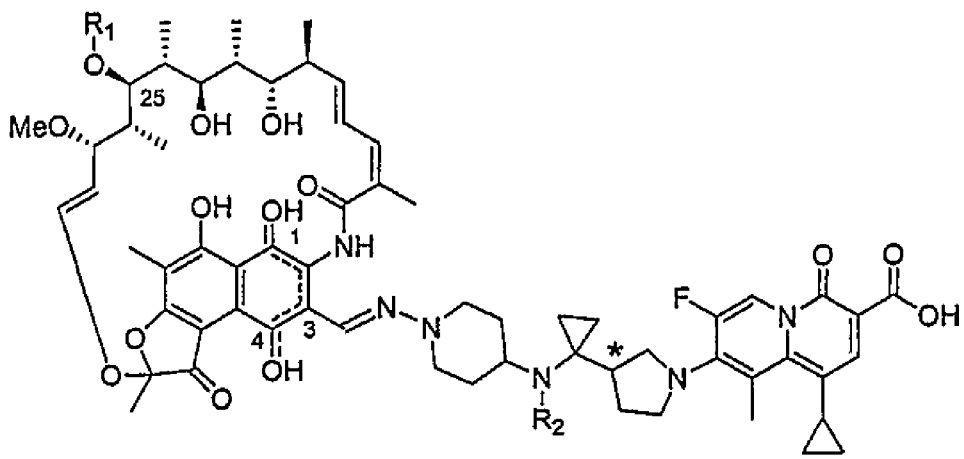

In Column 6, line 2, "SV" should be changed to --SV sodium--.

In Column 29, line 16 (lower structure on page), the structure should appear as follows:

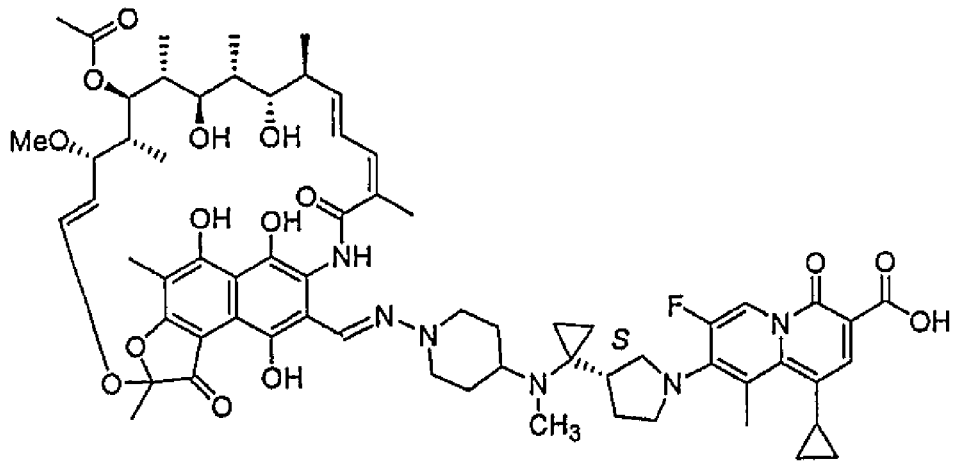

UNITED STATES PATENT AND TRADEMARK OFFICE
CERTIFICATE OF CORRECTION

PATENT NO.       : 7,226,931 B2
APPLICATION NO.  : 11/186425
DATED            : June 5, 2007
INVENTOR(S)      : Ding et al.

It is certified that error appears in the above-identified patent and that said Letters Patent is hereby corrected as shown below:

In Column 31, line 5 (upper structure on page), the structure should appear as follows:

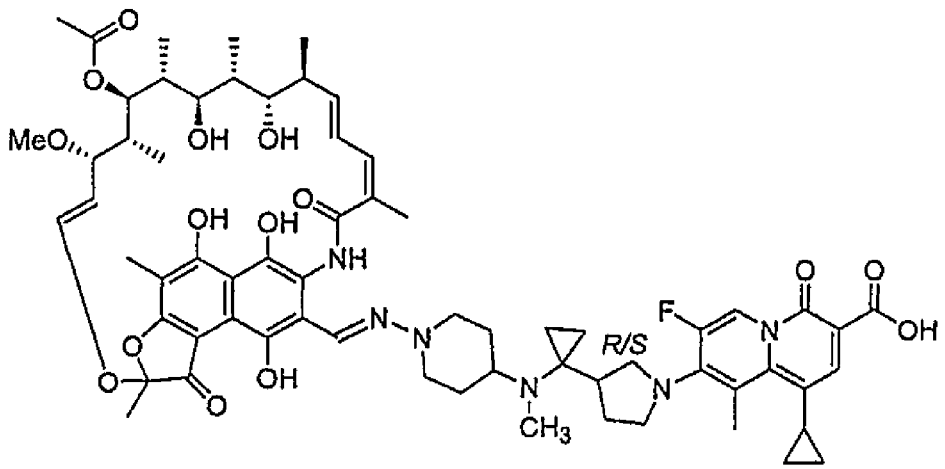

UNITED STATES PATENT AND TRADEMARK OFFICE
CERTIFICATE OF CORRECTION

PATENT NO.       : 7,226,931 B2
APPLICATION NO.  : 11/186425
DATED            : June 5, 2007
INVENTOR(S)      : Ding et al.

It is certified that error appears in the above-identified patent and that said Letters Patent is hereby corrected as shown below:

In Column 31, line 35 (lower structure on page), the structure should appear as follows:

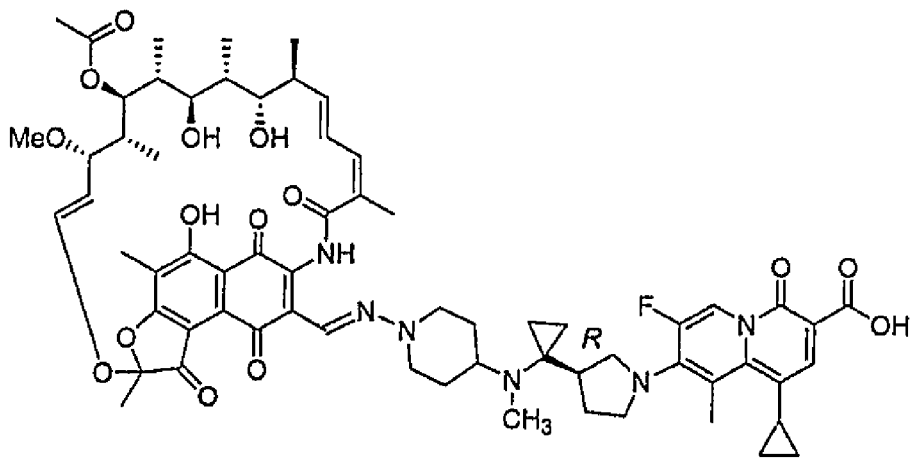

In Column 35, line 4, "SV" should be changed to --SV sodium--.

Signed and Sealed this

Sixteenth Day of October, 2007

JON W. DUDAS
*Director of the United States Patent and Trademark Office*